US009222906B2

(12) United States Patent
Youssi et al.

(10) Patent No.: US 9,222,906 B2
(45) Date of Patent: Dec. 29, 2015

(54) WIRELESS IN-KILN MOISTURE SENSOR AND SYSTEM FOR USE THEREOF

(71) Applicant: SCS Forest Products, Inc., Englewood, CO (US)

(72) Inventors: Patrick Youssi, Denver, CO (US); Scott Schneider, Highlands Ranch, CO (US)

(*) Notice: Subject to any disclaimer, the term of this patent is extended or adjusted under 35 U.S.C. 154(b) by 227 days.

(21) Appl. No.: 13/934,887

(22) Filed: Jul. 3, 2013

(65) Prior Publication Data
US 2014/0009174 A1  Jan. 9, 2014

Related U.S. Application Data

(60) Provisional application No. 61/667,942, filed on Jul. 4, 2012.

(51) Int. Cl.
  G01N 27/00  (2006.01)
  G01N 27/22  (2006.01)
  G01N 27/04  (2006.01)
  G01N 33/46  (2006.01)

(52) U.S. Cl.
  CPC ............ *G01N 27/223* (2013.01); *G01N 27/048* (2013.01); *G01N 33/46* (2013.01)

(58) Field of Classification Search
  CPC .... G01N 27/223; G01N 27/048; G01N 33/46
  See application file for complete search history.

(56) References Cited

U.S. PATENT DOCUMENTS

| | | |
|---|---|---|
| 3,807,055 A | 4/1974 | Kraxberger |
| 4,107,599 A | 8/1978 | Preikschat |
| 4,389,578 A | 6/1983 | Wagner |
| 4,580,233 A | 4/1986 | Parker et al. |

(Continued)

FOREIGN PATENT DOCUMENTS

| | | |
|---|---|---|
| CN | 101183486 | 5/2008 |
| WO | WO 2006/053392 | 5/2006 |

OTHER PUBLICATIONS

Simpson, William T., ed., Dry Kiln Operators Manual, Chapter 8: Drying Defects, U.S. Department of Agriculture, 1991, pp. 179-205.

(Continued)

*Primary Examiner* — Jeff Natalini
(74) *Attorney, Agent, or Firm* — Aspire IP; Yiu F. Au

(57) ABSTRACT

A wood monitoring system and method is disclosed for monitoring lumber characteristics (e.g., lumber moisture) in environments of extremely high and prolonged temperature and moisture, e.g., a kiln. The monitoring system and method includes:

(a) Sensors (provided within lumber stacks), wherein such sensors are battery powered and wirelessly communicate measurements indicative of moisture content of the wood adjacent to and/or between metal plates provided in an electrical circuit with the sensors and the wood between the plates;

(b) Computer implemented methods and systems for wireless communication that conserve sensor battery power such that the sensors can operate for, e.g., six months within extremely adverse temperature and moisture environmental variations; and (c) Computer implemented methods and systems for estimating moisture content with a wood/lumber stack, and for predicting such moisture content (e.g., as a substantially steady state within the wood) after drying completion.

20 Claims, 7 Drawing Sheets

(56) References Cited

U.S. PATENT DOCUMENTS

| | | | |
|---|---|---|---|
| 6,124,584 A | 9/2000 | Blaker et al. | |
| 6,281,801 B1 | 8/2001 | Cherry et al. | |
| 6,703,847 B2 | 3/2004 | Venter et al. | |
| 6,784,671 B2 | 8/2004 | Steele et al. | |
| 6,784,672 B2 | 8/2004 | Steele et al. | |
| 6,989,678 B2 | 1/2006 | Venter et al. | |
| 7,068,050 B2 | 6/2006 | Steele | |
| 7,068,051 B2 | 6/2006 | Anderson | |
| 7,146,747 B2* | 12/2006 | Studd et al. | 34/396 |
| 7,676,953 B2* | 3/2010 | Magill | 34/282 |
| 7,814,799 B2 | 10/2010 | Tiitta et al. | |
| 2003/0062908 A1* | 4/2003 | Venter et al. | 324/661 |
| 2004/0187341 A1 | 9/2004 | Studd et al. | |
| 2007/0107500 A1* | 5/2007 | Patel | 73/73 |
| 2008/0072448 A1 | 3/2008 | Hubig et al. | |
| 2008/0148593 A1 | 6/2008 | Tiitta et al. | |
| 2010/0225335 A1 | 9/2010 | Boschetti et al. | |
| 2011/0093217 A1 | 4/2011 | Kates | |
| 2012/0139565 A1 | 6/2012 | Ambuter | |

OTHER PUBLICATIONS

Anon, "Guides to practice in Corrosion Control: Corrosion of metals by wood," Corrosion Education and Training Working Party, Department of Industry and the Central Office of Information, London, UK, 1979, http://www.npl.co.uk/upload/pdf/corrosion_of_metals_by_wood.pdf, 17 pages.

Arganbright et al., "Laboratory Evaluation of Kiln Corrosion Caused by the Drying of Wetwood," 34th Western Dry Kiln Clubs Meeting, 1983, pp. 23-32.

International Search Report and Written Opinion for International (PCT) Application No. PCT/US13/49287 mailed Dec. 13, 2013 12 pages.

* cited by examiner

Fig. 4: WIRELESS SENSOR

Fig. 6
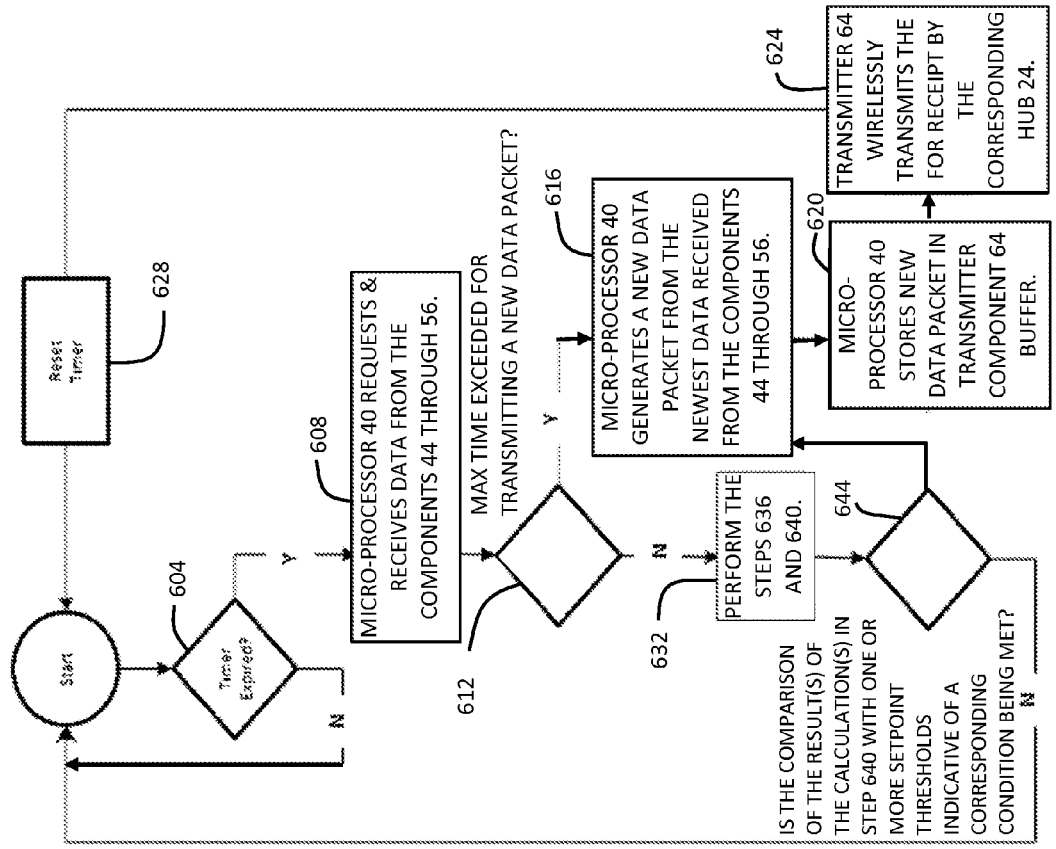
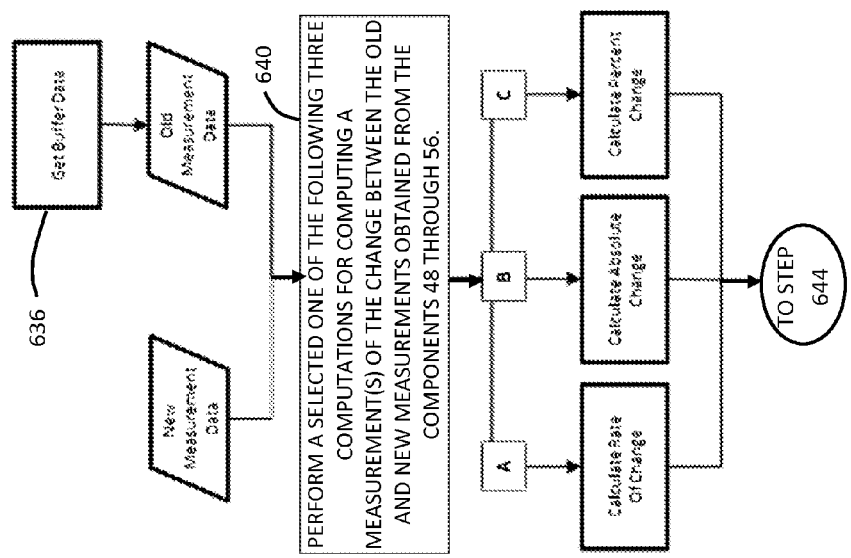

WIRELESS IN-KILN MOISTURE SENSOR AND SYSTEM FOR USE THEREOF

RELATED APPLICATION

The present application claims the benefit of U.S. Provisional Patent Application No. 61/667,942 filed Jul. 4, 2012, which is fully incorporated herein by reference.

FIELD OF THE INVENTION

The present invention is related to the wireless monitoring of drying of wood in a kiln, and more particularly, wireless sensors for monitoring the wood drying process wherein the life of the batteries for the sensors is extended.

BACKGROUND

Today's market for kiln dried lumber demands significantly greater attention to the lumber production process. Government and industry regulations and customer expectations of wood quality have increased every year. Additionally, competitive pricing of final lumber grade has become more severe. Therefore, mills must maintain a high level of scrutiny of each production stage to reduce or eliminate product errors and waste. Process mistakes that do occur result in wood products that have compromised strength properties, may be susceptible to mold, or can lose significant value due to shrinkage or any number of visual defects. In addition, wood processing errors can cause lost productivity as well as higher energy costs for a mill.

There are a number of vendors that provide in-kiln moisture measurement systems. In fact, prior art systems have been commercially available for two decades. Such prior art systems (e.g., by the manufacturers Wagner, Wellons, and Accudry, SCS Forest Products) have been described in significant detail in various public disclosures, including the following U.S. Pat. No. 4,389,578 by Wagner; U.S. Pat. No. 4,580,233 by Parker, et al.; U.S. Pat. No. 6,703,847 by Venter et al.; and U.S. Pat. No. 6,989,678 by Venter et al. each of which is fully incorporated herein by reference. Additionally, the following U.S. patent numbers are fully incorporated herein by reference: U.S. Pat. No. 3,807,055 by Kraxberger; U.S. Pat. No. 4,107,599 by Preikschat; U.S. Pat. No. 6,124,584 by Blaker et al.; U.S. Pat. No. 6,281,801 by Cherry et al.; U.S. Pat. No. 6,784,671 by Steele, et al.; U.S. Pat. No. 6,784,672 by Steele, et al.; U.S. Pat. No. 7,068,050 by Steele; and U.S. Pat. No. 7,068,051 by Anderson. U.S. Patent Application Publication No. US 2004/0187341 by Studd, et al. is also fully incorporated herein by reference.

All of these systems work using decades-old theory by converting capacitance response to moisture content. This is accomplished by placing two or more metal plates in a lumber stack, which are vertically separated by some calculated distance. The system then creates a capacitor by applying an electrical signal to the plates. The main dipolar constituent between the plates is water within the lumber stack. Therefore, the capacitance response diminishes during a drying cycle as water is removed. The drop in capacitance is correlated to the loss of moisture.

To-date, the prior art systems that perform the function of measuring the change in capacitance over time, have relied upon placing one or more fixed wall-mounted metering devices inside, outside or near the kiln for drying the lumber therein. The metering devices are responsible for determining the electrical response of the circuit formed by the metal (steel) plates and the lumber stack between the two plates. Cables connect the meters to the plates inserted in the lumber stack. The metering devices, in turn, are connected, via wire or cables, to a central programmable logic controller (PLC) or other computing device (e.g., a personal computer, PC herein). The calculation of moisture content is performed either at the meters themselves or at a central PLC or PC. These wired systems have been installed throughout lumber drying kilns in North America.

These prior-art lumber drying systems have a number of limitations. Since all of these systems are connected via cables to a main PC or controller, the number of meters is limited by financial constraints. In addition to the per-unit cost for each meter, conduit runs must be installed to protect cables that transmit electrical measurements to the PCL or PC. Depending on the configuration of the kiln, these conduit runs can be hundreds of feet long. Running high temperature cable inside aluminum conduit between each meter and the PLC or PC is a considerable upfront expense as well as an on-going maintenance expense.

Another limitation of such prior art lumber drying monitoring systems is that once a measurement point (e.g., meter) is fixed to the kiln wall and conduit is run to that point, the location cannot be easily changed without incurring significant cost. Therefore, the operator does not have flexibility to target desired locations in the kiln drying lumber. Often times, lumber mills will produce new lumber products that require greater in-kiln observation in the first number of manufacturing cycles. Installing additional moisture sensors in a timely manner is not an option. Therefore, mills will often incur costly production loss and greater energy usage in the early manufacturing runs until the manufacturing process has been standardized.

Finally, the entire lumber production industry is undergoing a significant shift as the industry moves from batch processing of lumber to continuous processing. Instead of packages of lumber being placed inside a kiln for a set period of time, operators are continuously moving the stacks of lumber on rail tracks through various heating chambers. Having measurement sensors within such lumber stacks wherein the sensors are tethered to meters of fixed location is not an option in this case. In particular, the lumber stacks may travel approximately 100 feet (or greater, e.g., 200 feet) through the various drying chambers. At any one time, there may be 10 or more distinct lumber stacks moving through the drying process. Moving cables attached to each lumber stack would create too many safety and logistical issues for the mills to consider this a viable option.

Regarding wireless technology, unfortunately, commercially available in-situ wireless moisture measurement sensors are not an option for a number of reasons. First, there are no viable wireless systems that can survive softwood kiln temperatures. In most cases, kiln temperatures reach 260° Fahrenheit (F.) or higher, which is far higher than conventional moisture sensor technology allows. Second, the kiln environment has very high humidity with hot ash and sap sticking to any available surface. Because of these conditions, very limited electronics have heretofore been provided inside the kiln. In particular, most commercially available electronics have a maximum temperature of 125° F. and are not effective for marine environments (e.g., where there is consistently high moisture content of, e.g., 90% or more). Further, in-kiln temperatures can range from −40 to +260° F., and this wide temperature range is especially problematic in that kiln temperatures can ramp from the low end of this range to the upper end of this range in a matter of hours (e.g., three to four hours or less). Furthermore, sensors (in the lumber stacks) and the meters placed in the kiln must operate continuously for, e.g., up to three weeks.

Moreover, if the moisture sensors within the lumber stacks are to be untethered (e.g., wireless) in their communications, then they must be powered by batteries. However, in general, battery life for electronic devices is severely degraded by the elevated kiln temperatures as recited above. In fact, studies show that batteries operating at temperatures above 113° F. will lose 50% of their useful operating life performing a task whereas at lower temperatures (e.g., 100° F.), there would only be a 20% to 30% reduction in such useful operating life. This is particularly important for the drying and processing of softwood lumber since such lumber may need to be monitored for lengthy time periods, e.g., approximately six months or longer in kiln environments with extremely high prolonged temperatures and/or extremely high prolonged moisture content. Accordingly, perhaps the most challenging for wireless lumber monitoring sensors is the battery life. This is probably the primary reason that no other manufacturer has developed a wireless sensor based capacitance system for the monitoring the moisture content of softwood within wood drying kilns since softwood lumber in-kiln drying requires sensor batteries to be operationally useful at prolonged temperatures of 260° F. (or higher)—significantly higher than the top range for standard batteries to effectively operate, e.g., a typical wireless sensor. In particular, such high temperatures may be required for up to twenty-one days. It is, however, worth mentioning that there are specialty batteries that operate at higher temperatures, but battery life would still be a significant issue.

Because there are no wireless options for the softwood market, meter suppliers have looked at creating physical connections using sleds instead of cables between the meters and the lumber stack. As the lumber stack moves past a fixed sled, the sensors within the lumber stack come into electrical contact (e.g., via a protrusion from each sensor contacting sled) the meter can make a valid measurement. There are a number of disadvantages with such sled systems, including, but not limited to installment cost, maintenance costs, accuracy and limited lumber moisture sampling ability due to the sleds being attached to the kiln wall. Accordingly, the adoption of these sleds has been very slow.

Due to the drawbacks (e.g., as recited above) with the prior art lumber drying monitoring systems for the lumber industry, the technology in the present disclosure has been developed for addressing such drawbacks, and in particular, providing an apparatus (e.g., one or more computational devices/equipment) and computer methods for monitoring lumber characteristics (e.g., moisture content), wherein wireless lumber measurements are taken by sensors embedded within lumber stacks and such sensors can remain operationally effective for extended periods of time without maintenance such as battery replacement.

Accordingly, it would be advantageous to have a lumber monitoring system and method that mitigates or cures the above-identified drawbacks of the current lumber drying systems and methods.

SUMMARY

A lumber monitoring system and method is disclosed hereinbelow for monitoring lumber characteristics (e.g., lumber moisture) in environments of extremely high and prolonged temperature and moisture. The present lumber monitoring system and method includes:
(a) Sensors (provided within lumber stacks), wherein such sensors are (1) battery powered and wirelessly communicate measurements indicative of, e.g., the moisture content of the wood adjacent to and/or between metal plates provided in an electrical circuit with the sensors and the wood between the plates, and (2) able to effectively operate in such extreme environments that vary from, e.g., from −40 to +260° F., with ambient moisture content ranging from extended durations near zero moisture to extended durations of 90% to 100% moisture;
(b) Computer implemented methods and systems for wireless communication that conserve sensor battery power such that such sensors can effectively operate for, e.g., six months within extremely adverse temperature and moisture environmental variations; and
(c) Computer implemented methods and systems for estimating moisture content with a wood/lumber stack, and for predicting such moisture content (e.g., as a substantially steady state within the wood) after drying completion.

In one embodiment of the presently disclosed system and associated method, the lumber monitoring equipment (including associated computer systems for performing various computations) can be configured for measuring attributes or characteristics of lumber prior to, during and after such lumber is processed within, e.g., a lumber drying kiln facility and/or another lumber processing facility such as a saw mill. In particular, such lumber attributes or characteristics are monitored so that the lumber's environment (e.g., in kiln environment) can be adjusted and/or maintained so that the lumber attains (and retains) a desired range of moisture content. Such lumber monitoring equipment may determine appropriate lumber moisture content ranges, wherein such ranges may be dependent upon, e.g., the type of wood, the current content of moisture, expected environmental conditions to which the lumber may be subjected, etc. Such monitoring equipment typically includes a PLC or PC (as these terms are defined above) having various specialized computer programmatic instructions for (a) controlling the wood monitoring process and (b) computing, e.g., estimated current wood moisture content and/or predicting a resulting substantially steady state moisture content within the wood after drying. Note that the hardware and software for performing (a) and (b) immediately above also will be referred to hereinbelow as a "controller".

The novel lumber monitoring system and method of the present disclosure provides a unique solution that limits battery usage by sensors, e.g., within lumber stacks. In particular, the following features are provided:
(a) Each such sensor only wirelessly transmits (to a wireless device identified as a "hub" or "hub device" herein) when capacitance within the lumber stack (within which the sensor is embedded) has changed by a predetermined amount (e.g. a percentage thereof), and
(b) Each such sensor wirelessly reduces the number of readings and wireless transmissions during less critical phases and increases the read rate and wireless transmissions when these readings are most important.

In particular, embodiments of the lumber monitoring equipment and associated method therefor increase battery performance such that empirical testing shows batteries can potentially last six months or more in a typical operating environment within a lumber drying kiln.

Another novel aspect of the present disclosure includes computer instructions (and/or dedicated computational machine device(s) implementing such instructions in hardware and/or software) for estimating moisture content using both capacitance and resistance. In particular, the present disclosure describes the creation and use of a unique index (Measurement Index herein) for assessing moisture content in lumber, wherein both capacitance and resistance are provided as inputs, and such inputs may be combined or weighted for estimating the moisture content in lumber. For example, at one or more time intervals (e.g., during the drying of lumber), resistance measurements are given an increased weight in the Measurement Index in comparison to capacitance measurements. In particular, capacitance is not as accurate as resistance at high moisture readings. However, as lumber dries, it has been determined that capacitance becomes far more accurate than resistance in measuring lumber moisture content. Thus, alternating current (AC) resistance measurements can be a good indicator of moisture content when wood is very wet since, e.g., large changes in resistance may be the result of small changes in moisture content while capacitance measurements are more indicative of wood moisture content when such moisture content is below, e.g., a range of fiber saturation point as one skilled in the art will understand. Therefore, the novel wood drying system and method models the wood drying process much more consistently and accurately when both capacitance and resistance are used.

Embodiments of the present wood drying system and method also provide for the wireless monitoring of wood moisture content. Further, such wireless monitoring can be performed in:

(1) A batch mode where the wood in a given batch is dried separately from other batches, or (2) A continuous mode where wood for various products is dried concurrently, albeit according to each product specifications; in particular, such continuous wood drying includes the movement of the stacks of wood between drying chambers.

It is also an aspect of the presently disclosed monitoring system that the wireless sensors used for such monitoring can be easily repositioned as desired for better monitoring the moisture content of the wood for the product intended. Moreover, it is within the scope of the presently disclosed wood monitoring system to allow various sensors to be wirelessly activated and deactivated by, e.g., a hub device with which a plurality of such sensors wirelessly communicate. Accordingly, wireless sensors may be distributed throughout a wood stack, and one or more of the sensors may be activated in response to, e.g., data received from a subset of the sensors. In particular, a PLC or PC performing the computations for converting received sensor data (obtained via one or more hub devices, likely at fixed locations along the wood/lumber processing or drying path) may determine whether sensor data from additional sensors within a wood stack should be activated.

It is a further aspect of an embodiment of the presently disclosed monitoring system that such a PLC or PC has access to mapping data which indicates the locations of the sensors within the wood/lumber stack. In one embodiment, each sensor may be wirelessly located within its wood stack and/or relative to other sensors so that a data map of the sensors within the wood stack can be generated and used for selectively activating and/or deactivating various sensors (subsets thereof) depending on the sensors location within it stack (or more generally in the kiln), and/or wood monitoring data received from, e.g., a particular subset of the sensors. In one embodiment, disjoint subsets of sensors may be activated and deactivated throughout the storage and processing of a wood/lumber stack (i.e., while being dried in a kiln, being stored after or before drying, being processed after being dried) for determining the moisture within the wood. Such disjoint subsets of sensors may provide the following advantages: (1) the battery life of each sensor is extended since its subset is only activated occasionally, (2) if each sensor subset is distributed differently but still is able to provide monitoring data for the entire wood/lumber stack, then the various sensor views of, e.g., moisture within the wood/lumber stack from the various sensor subsets can provide greater assurance that the wood/lumber is being properly processed and/or maintained, and (3) the sensor subsets provide a failsafe ability to the monitoring process in that one or more failed sensors may be tolerated due to the plurality of views of the wood/lumber provided by multiple sensor subsets. Accordingly, the PLC or PC (referred as a "controller" hereinbelow) may perform such selective activation and/or deactivation via wireless transmissions to the sensors activated or deactivated.

In one embodiment of the presently disclosed monitoring system, the positions of the sensors within a wood/lumber stack are determined relative to one another, relative to another location, or as an absolute location (e.g., via GPS). Accordingly, the presently disclosed monitoring system can detect an unintended dislocation of a sensor relative to other sensors, and adjustments may be made in the monitoring of the wood/lumber and/or an operator may be alerted to, e.g., reposition the dislocated sensor.

Since lumber drying kiln operators can deploy as many of the presently disclosed measurement sensors as required for the specific wood product being produced, in some cases, mills may add, subtract or reposition sensors within a wood stack between kilns to provide improved sampling in a particular kiln. Note that since various kilns may have substantially different wood drying characteristics (e.g., heat flow patterns, heat gradients, air circulation, and venting) such repositioning of sensors may be dependent upon the kiln within which the wood stack is provided. Additionally/optionally, a plurality of sensor subsets may be provided in the wood stack so that one or more sensor sets may be activated dependent upon the particular kiln in which the wood stack having the sensor subsets is provided.

Moreover, in one embodiment of the presently disclosed monitoring system, the number, location and/or activation of sensors within a wood stack also can be dependent upon the type of wood. Some wood/lumber products can be more variable in their moisture content within a wood drying kiln. In particular, additional moisture content sensor data samples may be needed to fine tune the wood drying process. In other wood/lumber products being dried, the wood/lumber moisture content may be more evenly distributed; thus fewer sensors (or activations thereof) may be required to make (1) an accurate prediction of the current moisture content of a wood stack, and/or (2) make a prediction of what the moisture content of the wood stack will be after drying (assuming, e.g., the wood stack is stored or processed in a manner that is amenable to such prediction).

It is a further aspect of the wood sensors disclosed herein that they have a reduced susceptibility to corrosion from the drying of wood. In particular, such sensors are subjected to potentially corrosive substances in wood ash and sap. Note, it is well known that wood is corrosive by nature and can be made more corrosive by various treatments. In particular, wood includes acetic acid which is volatile, and in an ill-vented space (such as in a kiln), wood can cause metal corrosion; further, wood ash includes from 0.2 to 4% of mineral ash, which consists largely of calcium, potassium and magnesium as carbonate, phosphate, silicate, and chloride; aluminum, iron and sodium are also present. Sulphate contributes 1 to 10% of wood ash by weight, and chloride 0.1 to 5%, and these two radicals augment the corrosive action of the acetic acid.

Accordingly, embodiments of the wood monitoring system and method herein may provide the following benefits:

1. Since the hub(s) need not be tethered to the sensors, such hub(s) can be flexibly located inside or outside the kiln from which the hub(s) receive wireless sensor transmissions. In particular, such hub(s) need only be able wirelessly communicate with the sensors and also transmit data (e.g., via a cable) to the controller (as this term is described above). Thus, such hub(s) need only be placed in wireless range for communicating with the sensors in the kiln associated with hub(s). Thus, such hubs may be positioned in a mill yard, sawmill, planer mill, etc. That is, the hub devices are no longer limited to being located in the kilns. Also, since such hub devices can be positioned virtually anywhere along a wood processing path (e.g., within a saw mill), real-time monitoring of wood moisture content can be determined where heretofore such has not been possible.
2. When a sensor's battery potential reduces below, e.g., a predetermined threshold, the frequency of data transmissions may be reduced to conserve the battery.
3. In one embodiment, the controller is provided with data indicative of critical wood drying intervals for a wood stack. Accordingly, the controller may instruct the sensors within the wood stack to reduce their moisture sampling rates outside of such critical intervals to thereby extend the sensors' effective battery life. Note that such critical intervals may be based on historical wood/lumber drying for the type of wood/lumber being currently kiln dried, and/or the particular kiln being used for the drying, and/or the kiln settings (e.g., timing of heat applied, venting, circulating fans activated, etc.).
4. More accurate and reliable moisture content estimation is achieved by using both capacitance and resistance to estimate wood/lumber moisture content as discussed hereinabove.
5. The sensors have a reduced susceptibility to wood product corrosion.

In one embodiment, the present disclosure is directed to a method for monitoring the moisture content of a collection of wood members (e.g., lumber) drying in a kiln, the kiln operable for applying heat, and air circulation for drying the collection to a specified moisture content, wherein:

There is a wireless sensor in operable contact with the wood collection for forming an electrical circuit with the wood, wherein the circuit additionally includes two spaced apart conductive plates positioned within the wood collection, and wherein the sensor and the circuit are configured to establish each of a capacitance and resistance of a water content of at least a portion of the collection, the portion residing between the spaced apart conductive plates; and wherein the sensor includes: (a) a wireless transmitter for wirelessly communicating with a stationary device, the stationary device for wirelessly receiving data from the sensor related to the water content of the portion of the collection, the data including measurements of the capacitance and resistance, and (b) one or more batteries for providing electrical power to the sensor;

wherein the method performs the following steps by computational machinery:

(a) activating a timer for determining when a first time limit is exceeded;

(b) obtaining an instance of the data during the first time limit;

(c) determining a value indicative of a change between the instance and a previous instance of the data;

(d) comparing the value to a predetermined change related condition indicative of particular changes between instances of the data;

wirelessly transmitting the instance to the device, via the wireless transmitter, when the comparing step yields a first result indicative of the predetermined change related condition occurring between the one instance and the previous instance, and not wirelessly transmitting the instance when the comparing step yields a second result indicative of the predetermined change related condition not occurring between the one instance and the previous instance;

wirelessly transmitting a further instance of the data to the device, via the wireless transmitter, when the first time limit is exceeded;

(e) evaluating a predetermined condition, wherein the evaluation of the predetermined condition performs one of: (i) a comparison of an elapsed time for drying the collection in the kiln with a predetermined elapsed time limit for drying the collection in the kiln, (ii) a comparison of a humidity in the kiln with a humidity threshold, or (iii) a comparison of an impedance for the portion of the collection with an impedance threshold;

(f) obtaining, when the predetermined condition evaluates to a predetermined result, information for a second time limit different from the first time limit;

(g) using the information for activating the timer to determine when the second time limit is exceeded; and (h) wirelessly transmitting a second instance of the data to the device, via the wireless transmitter, when the second time limit is exceeded;

wherein for conserving the batteries, the first time limit is longer than the second time limit.

In a related embodiment, the present disclosure is directed to a wireless sensor for monitoring the moisture content of a collection of wood members (e.g., lumber) being dried in a kiln, the kiln operable for applying heat, and air circulation for drying the collection to a specified moisture content, wherein the wireless sensor is in operable contact with the wood collection for forming an electrical circuit with the wood, wherein the circuit additionally includes two spaced apart conductive plates positioned within the wood collection, and wherein the sensor and the circuit are configured to establish capacitance and resistance of a water content of a portion of the collection, the portion residing between the spaced apart conductive plates; the sensor including:

(a) one or more batteries for electrically powering the sensor;

(b) a wireless transmitter for wirelessly communicating with a stationary device, the wireless communications including transmissions by the transmitter of data related to the water content of the portion of the collection, the data including measurements of each of the capacitance and resistance, measurements of the humidity in the kiln, and measurements of a temperature in the kiln;

(c) a processor for iteratively: (i) obtaining one of the measurements of the capacitance, one of the measurement of the resistance, one of the measurements of the humidity, and one of the measurements of the temperature, and (ii) providing the one measurement of each of:

the capacitance, resistance, humidity and temperature to the wireless transmitter for wirelessly transmitting as an instance of the data;

(d) a timer for determining when a first time limit is exceeded;

wherein one of the instances of the data is obtained by the processor during the first time limit;

wherein the processor obtains a value indicative of a change between the one instance and a previous instance of the data;

wherein the processor compares the value to a predetermined change related condition for identifying specific changes between instances of the data, and thereby obtaining one of: a first result indicative of the predetermined change related condition occurring between the one instance and the previous instance, and a second result indicative of the predetermined change related condition not occurring between the one instance and the previous instance;

wherein the wireless transmitter wirelessly transmits the instance to the device when the first result is obtained, and does not wirelessly transmit the instance when second result is obtained;

wherein the wireless transmitter wirelessly transmits a further instance of the data to the device when the first time limit is exceeded;

wherein the processor evaluates a predetermined condition, the evaluation of the predetermined condition performs one of: (i) a comparison of an elapsed time for drying the collection in the kiln with a predetermined elapsed time limit for drying the collection in the kiln, (ii) a comparison of a humidity in the kiln with a humidity threshold, or (iii) a comparison of an impedance for the portion of the collection with an impedance threshold;

wherein the processor obtains, when the predetermined condition evaluates to a predetermined result, information for a second time limit different from the first time limit;

wherein the processor uses the information for activating the timer to determine when the second time limit is exceeded;

wherein the wireless transmitter wirelessly transmits a second instance of the data to the when the second time limit is exceeded;

wherein for conserving the batteries, the first time limit is longer than the second time limit.

This Summary section is neither intended to be, nor should be, construed as being representative of the full extent and scope of the present disclosure. Additional benefits, features and embodiments of the present disclosure are set forth in the attached figures and in the description hereinbelow, and as described by the claims. Accordingly, it should be understood that this Summary section may not contain all of the aspects and embodiments claimed herein.

Additionally, the disclosure herein is not meant to be limiting or restrictive in any manner. Moreover, the present disclosure is intended to provide an understanding to those of ordinary skill in the art of one or more representative embodiments. Thus, it is important that the embodiments herein be regarded as having a scope including constructions of various features of the present disclosure insofar as they do not depart from the scope of the methods and apparatuses consistent with the present disclosure. Moreover, the present disclosure is intended to encompass and include obvious improvements and modifications of the present disclosure.

BRIEF DESCRIPTION OF THE DRAWINGS

FIG. 6: is a flow chart describing the logic used to conserve battery in a wireless sensor 20. In this case, transmissions are reduced by only transmitting when certain conditions have been met.

DETAILED DESCRIPTION OF THE INVENTION

Figure 2:
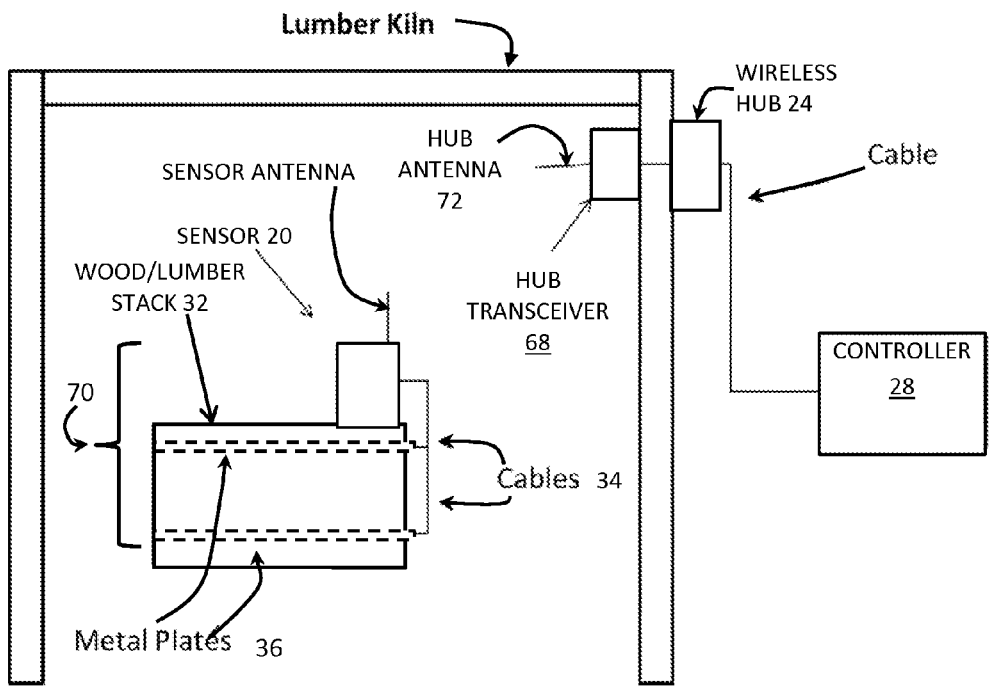
FIG. 2 shows a vertical cross section through an embodiment of a novel wireless in kiln lumber monitoring system according to the present disclosure.
Figure 3:
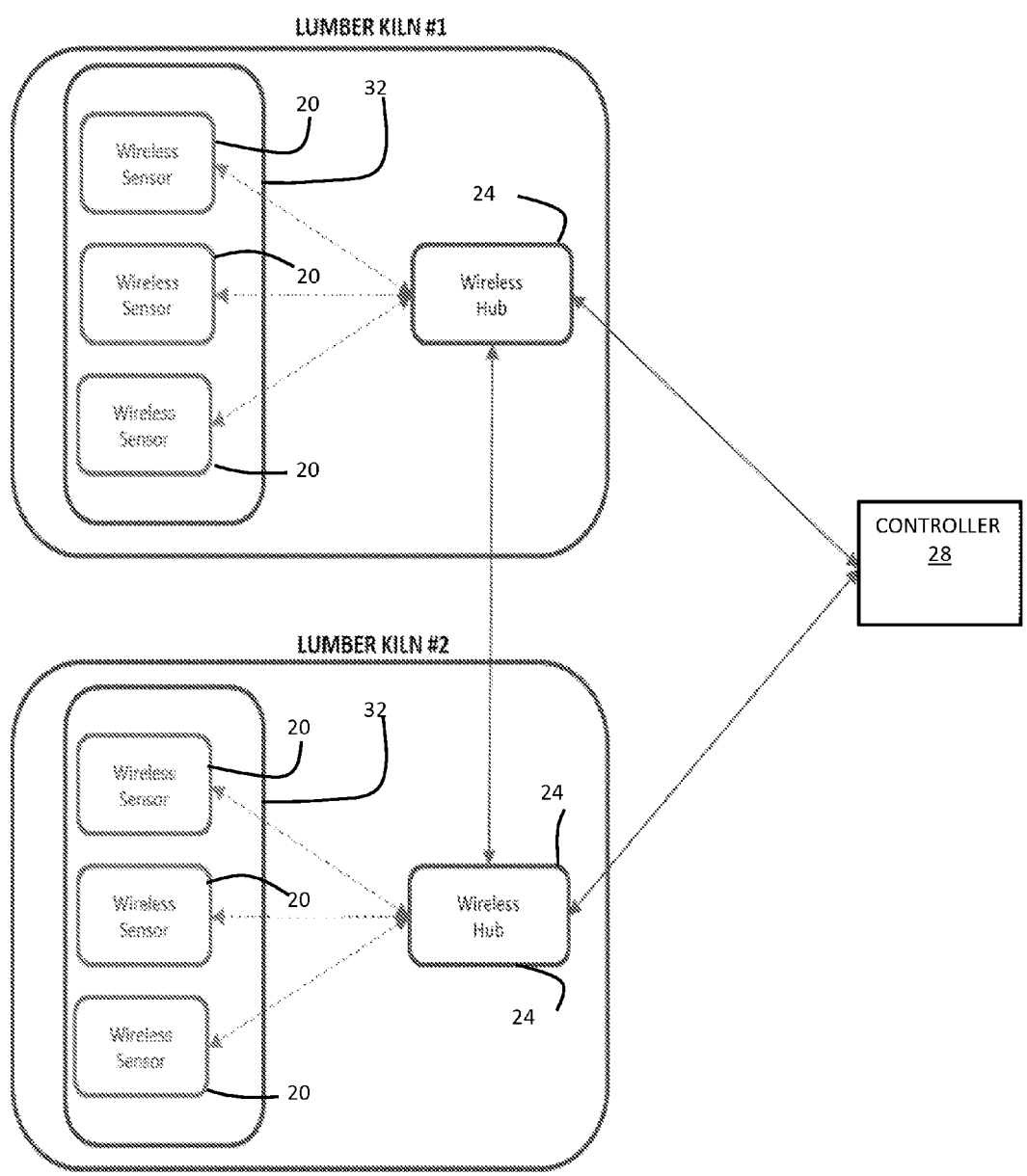
FIG. 3: is a block diagram showing the major system components.

FIGS. 2 and 3 illustrate embodiments of the lumber monitoring system and method as configured in a typical lumber mill. The main components are the wireless sensors 20, the wireless hubs 24 (also referred to as "hub devices" hereinabove and below) and a controller 28. Although only three sensors 20 are illustrated in FIG. 3 as residing in each of the stacks 32, this is only for illustrative purposes. In general, a substantially larger number of sensors 20 may be distributed within a corresponding wood/lumber stack 32 for collecting, e.g., wood/lumber capacitance and resistance data related to the moisture content of the stack 32. Each of the sensors 20 wirelessly communicates with a corresponding hub 24 for transmitting, e.g., the following data to the corresponding hub 24:

(1) a sensor 20 identifier (for identifying each sensor 20 uniquely), (2) capacitance and resistance data indicative of the moisture content in the stack 32, (3) measurements indicative of remaining battery power.

Other data values transmitted to its corresponding hub 24 (and subsequently transmitted to the controller 28) are disclosed in Appendix A hereinbelow).

Note that the sensors 20 are preferably distributed within or about the stack 32 according to a known configuration that may be based on: (a) the wood type in the stack 32, (b) an indication/estimation of wood moisture, and/or (c) characteristics of the kiln itself (as discussed in the Summary section hereinabove). More particularly, as shown in FIG. 2, each sensor 20 may be attached, via cables 34, to a unique pair of metal plates 36 (in some embodiments, a single cable 34 is connected to just one of the metal plates 34 with the other metal plate 36 being grounded), this pair being referred to herein as being "associated" with its sensor 20. The metal plates 36 are spaced apart within the wood/lumber stack 32, generally in a vertical direction; however they may be spaced apart horizontally as well. The associated pair of metal plates 36 is used to provide its sensor 20 with electrical properties related to the wood/lumber residing between these metal plates, and more particularly, information indicative a capacitance and resistance of the wood/lumber between these metal plates. A description of the use of such capacitance and resistance for determining the moisture content of the wood/lumber by the sensor 20 is provided in Appendix A hereinbelow. Related discussions of the use and computation of wood moisture content is provided in, e.g., various U.S. patents such as some of those recited above, and more particularly, U.S. Pat. No. 7,676,953 (the '953 patent herein) assigned to Signature Control Systems, Inc. which is also fully incorporated by reference herein.

Figure 1:
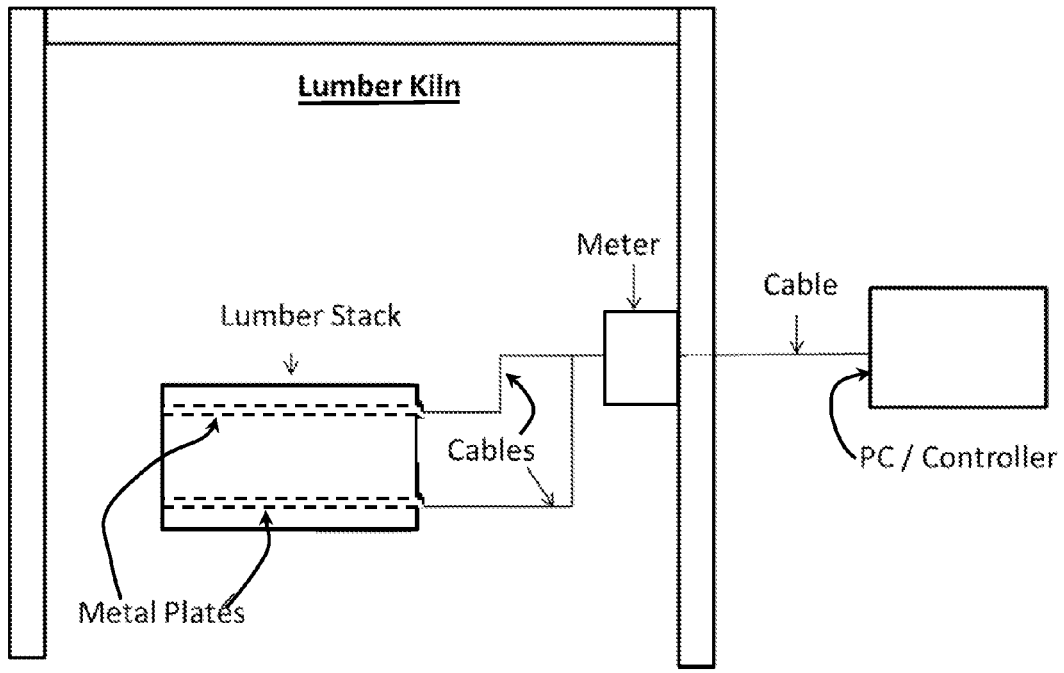
FIG. 1 is an illustration of a vertical cross section through a prior art lumber kiln moisture system, wherein a kiln for drying lumber is shown having a lumber stack therein, and the stack has spaced apart metal plates inserted therein. Each of the metal plates is tethered to a kiln wall mounted meter for obtaining, e.g., capacitance and resistance measurements indicative of the moisture content of the lumber between the metal plates. Accordingly, such prior art meters perform the processing provided herein by the novel sensors 20 (FIG. 2). However, since the wood/lumber stack is tethered to the wall of the kiln, the stack cannot be moved without disconnecting the cables from the meter. Moreover, the moisture in the wood/lumber stack can only be monitored where such a meter is in close proximity for connecting the cables thereto.

The sensors 20 offer substantially more flexibility in monitoring wood moisture over prior art systems having a "meter" attached to the kiln wall as shown in FIG. 1. Since the sensors 20 are each wireless, each such sensor can be transported with the wood/lumber stack 32 without connecting and disconnecting cables. Thus, such sensors 20 and their associated cables 34 and metal plates 36 can be attached to their wood/lumber stacks 32 prior to the stack entering the kiln, and can remain with the stack after the kiln drying process is complete to thereby continue to monitor the moisture in the stack if desired.

Various configurations of the sensors 20 (and their associated metal plate 36 pairs) may be provided within a wood/lumber stack 32. In one embodiment, a first row of the sensors 20 may be distributed, evenly spaced, in (or about) the stack 32 substantially around a horizontal perimeter of the stack at a first height relative to the stack (e.g., at or near the top of the stack as illustrated in FIG. 2), wherein for each of the sensors 20, its associated metal plate 34 pair is approximately adjacent to its sensor 20, and such that this sensor is operably attached to (or contacting) the stack 32 in a manner that allows this sensor to, e.g., determine a local humidity of the air adjacent to this sensor, and determine a local temperature adjacent to this sensor which is indicative of at least one of: the wood/lumber at the sensor 20 or the air temperature thereabout. Since the spacing of the metal plates 36 within the stack 32 is likely to be no more than six to eight feet (and possibly substantially less), depending on, e.g., the height of the stack 32, a copy of the first row of sensors 20 (and their associated metal plate 34 pairs) may be provided as a second row of sensors 20 wherein this second row is provided at a different height relative to the stack. In particular, the first row of sensors 20 may be near or at the top of the stack 32, and the second row may be positioned below the first row an effective distance so that the sensors can reliably collect capacitance and resistance data for the wood between corresponding vertically aligned metal plate 34 pairs associated with each of the sensors 20 (e.g., without electrical interference from another sensor and its associated metal plate 36 pair. Since the wood/lumber stack 32 may be as much as 12 feet high, a plurality of instances of the first and second sensor rows may be provided in the stack at spaced apart vertical intervals. Note that the sensors 20 and the wireless hubs 24 for wirelessly communicating therewith (such sensors 20 and their hub 24 referred to herein as "corresponding" herein) may wirelessly communicate according to any one of the conventional wireless communication protocols such as WIFI, Bluetooth and any other protocol of a wireless frequency as allowed by law as one of ordinary skill in the art will understand.

The controller 28 may be connected to each of the wireless hubs 24 via a cable or wire (illustrated as a double headed arrow in FIG. 3 and identified as a cable in FIG. 2). Although two hubs 24 are shown in FIG. 3 as communicating with the controller 28, such a controller can be in signal communication with only one hub 24 or a relatively large plurality of hubs 24 (e.g., 15 to 30 meters or more). In one embodiment, the controller 28 may be collocated with one of the hubs 24. The communication between a controller 28 and a hub 24 is two-way to thereby enable, e.g., (1) sensor data (obtained by the hub 24 from corresponding wireless sensor 20 transmissions) to flow from the hub to the controller, and (2) controller 28 commands to be transmitted to the hub 24 and its corresponding sensors 20 (with which the hub wirelessly communicates) for controlling both the hub and such sensors 20. In one embodiment, the wired or cable connection between a hub 24 and the controller 28 is via an Ethernet cable run in conduit as one skilled in the art will understand.

FIG. 3 also illustrates an embodiment where there is an exchange of information between the hubs 24 themselves (e.g., via wireless communications such as WIFI or Bluetooth, or an Ethernet cable connection) as illustrated by the double headed arrow between the two illustrated hubs 24. Such communication between hubs 24 allows these hubs to be daisy-chained so that data can be sent from hub to hub (e.g., for a potentially large number of hubs such as twenty hubs). Accordingly, when the hubs 24 are daisy-chained, the direct connection between, e.g., the hub in kiln #2 and the controller 28 can be dispensed with if the hub 24 in kiln #1 is configured to transfer designated communications between the hub 24 of kiln #2 and the controller 28. Assuming such a daisy-chain configuration includes wireless communications between the hubs 24, such a configuration may limit the cost of the present wood monitoring system by reducing the amount of conduit that must be run for providing communications between the controller 28 and the plurality of hubs 24 operably controlled by this controller.

Hubs 24 may be located on the outside of a kiln having sensors 20 corresponding to the hub. The number of hubs 24 per kiln may be determined by the size and/or design of the kiln. For typical batch kilns, (e.g., kilns that dry all the wood in the kiln according to a single drying method where all the wood is moved into the kiln prior to kiln operation for drying the wood, and all wood in the kiln is moved out of the kiln only after all the wood is dried), one hub 24 may be placed in a location amenable for effective wireless communications with all the sensors 20 in the kiln. However, depending on the wireless environment, e.g., within the kiln, additional hubs 24 may be distributed about the kiln.

The wireless sensors 20 attached to a wood stack 32 can be grouped. The highest grouping typically will include all the sensors 20 residing in a single stack 32, or if the kiln is a batch kiln, all the sensors 20 residing in the kiln. Subgroupings or subsets (as discussed hereinabove) may be provided. Each sensor 20 in a group (or subset) wirelessly transmits data to a single predetermined corresponding hub 24. Each group of sensors 20 may monitor a single kiln or a chamber within a kiln; however, a single stack 32 also may be monitored. When a hub 24 receives data from its corresponding sensors 20, the hub will, in turn, put the data in a buffer and subsequently relay the data to the controller 28. Once the data is received by the controller 28, the controller stores the data in a database (not shown). Note, although not shown in FIG. 3, the sensor data may be displayed to an operator accessing the controller 28 so that the operator can monitor the wood drying process in substantially real-time.

Figure 4:
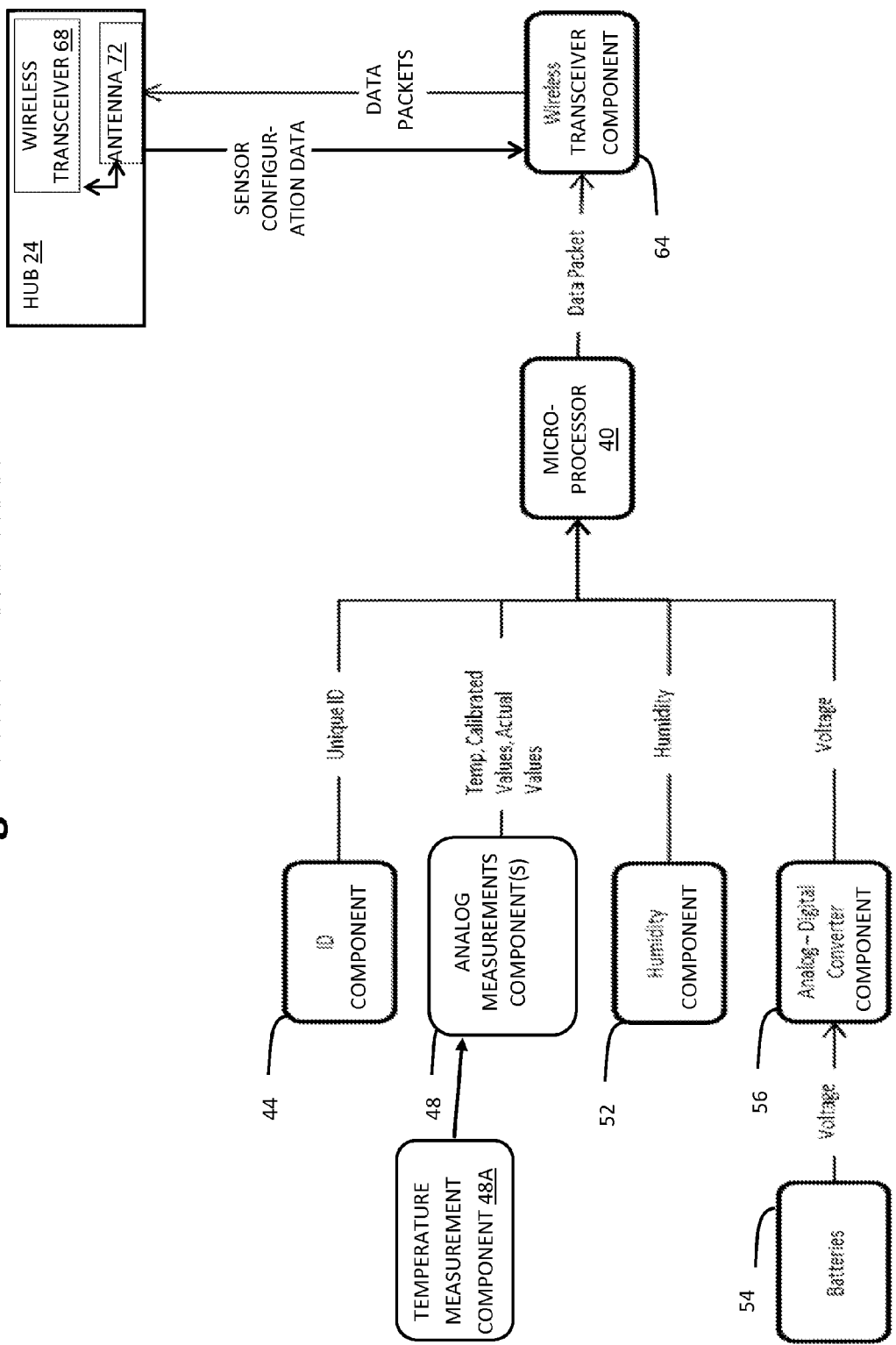
FIG. 4: is a block diagram showing the components of the wireless moisture sensor.

FIG. 4 shows a high level embodiment of a sensor 20. The sensor 20 includes a micro-processor 40 having firmware installed therein for performing at least the following tasks: (i) transmitting stack 32 moisture related data, e.g., when such data has changed in some meaningful way, and (ii) changing the moisture data sampling rate, e.g., the sample rate may be reduced during "non-critical" wood drying stages). Both of these aspects are described in more detail below.

The sensor 20 further includes the following components (each such component may be an integrated circuit more commonly known as a chip):

(a) An ID component 44 which may be a programmable EPROM or other silicon based component for storing identification data. The ID component 44 outputs, when requested by the micro-processor 40, identification data that uniquely identifies the sensor 20 from all other sensors 20.

(b) An analog measurements component(s) 48 which may be impedance chip AD5934 by Analog Devices, Inc., One Technology Way, Norwood, Mass. 02062-9106 (USA). The analog measurements component(s) 48 receives input from: (i) a temperature measurement component 48a (e.g., the AD5934 chip above also has an embedded temperature sensor). Further, the analog device component 48 determines capacitance and resistance electrical measurements corresponding to a moisture in the drying wood between the associated metal plates 36 for this sensor 20.

Regarding capacitance and resistance measurements, the analog measurements component(s) 48 determines capacitance measurements according to the disclosure in Appendix A provided hereinbelow.

(c) A humidity component 52 which may be a relative humidity sensor such as model number HTS2030SMD by Measurement Specialties, Inc., 1000 Lucas Way Hampton, Va. 23666 (USA). The humidity component 52 outputs, on request from the micro-processor 40, a measurement of the ambient humidity at the sensor 20.

(d) One or more batteries 54 for providing electrical power to the components of the sensor 20.

(e) An analog-digital converter component 56 which may be a micro-processor from the SAM4L family of microcontrollers by Atmel Inc., 1600 Technology Drive, San Jose, Calif. 95110 (USA). The analog-digital converter component 56 receives analog electrical signal input from the battery 54 indicative of the useful additional life in the battery for powering the sensor 20. In one embodiment, the output from the battery 54 may be a current measurement or a voltage. Upon request from the micro-processor 40, the analog-digital converter 56 outputs digital data corresponding to the input received from the battery as one skilled in the art will understand.

(f) A wireless transceiver component 64 which may be a radio transceiver or transmitter by Micrel, Inc., 2180 Fortune Drive, San Jose, Calif. 95131 (USA), model number: P/N MICRF405YML operating at 900 MHz. Upon receiving an output data packet from the micro-processor 40, the wireless transceiver component 64 wirelessly transmits the data packet to the hub 24 to which the sensor 20 corresponds. A wireless transceiver 68 and antenna 72 (FIG. 2) in the hub 24 receives the wireless data packet.

At certain designated times (or time intervals) while wood/lumber in-kiln drying is proceeding, the micro-processor 40 requests and receives data from each of the following components: the ID component 44, the analog measurements component(s) 48, the humidity component 52, and the AD (analog to digital) component 56. Once the data has been received from each of these components, the information is assembled into a data packet and provided to the wireless transceiver component 64 for wireless transmission to the hub 24 corresponding with the sensor 20.

For generating a data packet, the micro-processor 40 requests information from the components 44 through 56. Subsequently, the micro-processor 40 receives from the ID component 44, hexadecimal sensor identification data that uniquely identifies the sensor 20. The identification data is transmitted to the hub 24 with every data packet generated by the micro-processor 40 for identifying the source sensor of the data. For each data packet generated, preferably, the micro-processor 40 also obtains output from the analog measurements component(s) 48. As described above, the analog measurements component(s) 48 measures capacitance, resistance and temperature, and at least for the capacitance and resistance value, calibration values provided by the micro-processor 40 are used, wherein such calibration values are well known in the art for calibrating capacitance and resistance of the wood between the metal plate 34 pairs connected to the sensor 20. The calibration values are used by the analog measurements component(s) 48 to reduce or substantially entirely factor out extraneous capacitance and resistance values not indicative of the wood/lumber between the metal plate 34 pair associated with the sensor 20. In particular, for the electrical circuit 70 (FIG. 2) of the sensor 20, the attached cable(s) 34, the associate metal plate 34 pair, and the wood/lumber between these metal plates 34, the calibration values are used to remove, or substantially reduce, from the capacitance and resistance measurements, factors such as the capacitance and resistance of the cables 34 so that the capacitance and resistance values output by the analog measurements component(s) 48 to the micro-processor 40 substantially are only indicative of the moisture in the wood/lumber between the metal plates 36 associated with the sensor 20.

Additionally, the micro-processor 40 obtains from the humidity component 52 the relative humidity of the ambient air surrounding the sensor 20 for also providing in each generated data packet. Finally, an analog to digital component 56 is utilized to calculate a digital value of the voltage level of the batteries 54 and such calculated voltages are provided to the micro-processor 40 for inclusion in each data packet.

For a given collection of data from the components 44, 48, 52, and 56 (the data obtained for a same time), the micro-processor 40 generates a corresponding data packet that includes the content of the collected data. Note, that the micro-processor 40 includes a timing component (e.g. firmware), well-known in the art, for programmatically determining when to request and collect the data from the components 44, 48, 52, and 56. The timing component can be modified by commands from the controller 28, wherein such modifications may be:

(1) for setting a time interval between data collections from the components 44, 48, 52, and 56 (and substantially immediate transmissions of the corresponding resulting data packet to the controller 28, via wireless transmission to the hub 24), (2) for setting a range for at least one value from the collected data, wherein if the at least one value is outside of the range, then subsequent data collections are performed at a different frequency (e.g., a greater or lesser frequency as may be determined by communications from the controller 28, (3) setting different frequencies for collecting data from the components 44, 48, 52, and 56; for example, if the sensor's battery is low and it is not expedient to replace the battery or provide another proximate sensor 20 in the near term (e.g., due to the sensor 20 being not easily accessible), then unless a wood drying anomaly is detected, the sensor may conserve battery power by the micro-processor 40 only obtaining data input from a subset of the components 44 through 56 for at least some instances of the data packets generated and transmitted.

Note that in one embodiment, some of the components 44, 48, 52, and 56 may not be included in the sensor 20. In particular, in one embodiment, the humidity component may not be provided. Instead, humidity data may be obtained separately from the sensors 20, and communicated to the controller 28. Moreover, in one embodiment, the sensor 20 may also include an acoustic component for capturing particular sounds associated with the drying of wood such as wood cracking, shifting, and/or warping, etc. Accordingly, data from such an acoustic component can be also collected and provided in the micro-processor generated data packet for transmission to the controller 28.

In one embodiment, the hub 24 and each of its corresponding sensors 20 (plus possibly other sensors 20 whose wireless transmissions the hub can detect) may communicate asynchronously (or substantially so) on different wireless frequencies. Accordingly, there is little likelihood of collisions of data packets at the hub 24. However, since there may be a large plurality of sensors 20 (e.g., 20 or more) corresponding with the hub 24 for asynchronous wireless communication therewith, the additional hub and sensor electronics (and corresponding cost thereof) for allowing wireless communications between the hub 24 and each of its corresponding sensors 20 to occur on distinct wireless frequencies may be cost prohibitive in at least some embodiments. Thus, in an alternative embodiment, a predetermined small number of wireless frequencies may be utilized for communication between the hub 24 and its corresponding sensors 20. In this alternative embodiment, when a sensor's wireless transceiver component 64 receives a data packet from the sensor's micro-processor 40, the component 64 wirelessly transmits the data packet repeatedly; e.g., the data packet may be transmitted at three randomly determined times. Sending each data packet randomly three (or more) times is believed to substantially assure each data packet from the sensor 20 is accurately received by the associated hub 24 such that wireless transmissions by other sensors 20 do not interfere with wireless reception by the hub 24 of transmissions by the present sensor. Note that since each data packet has a unique timestamp, any duplicate copies of a data packet received by a hub 24 can be deleted.

Figure 5:
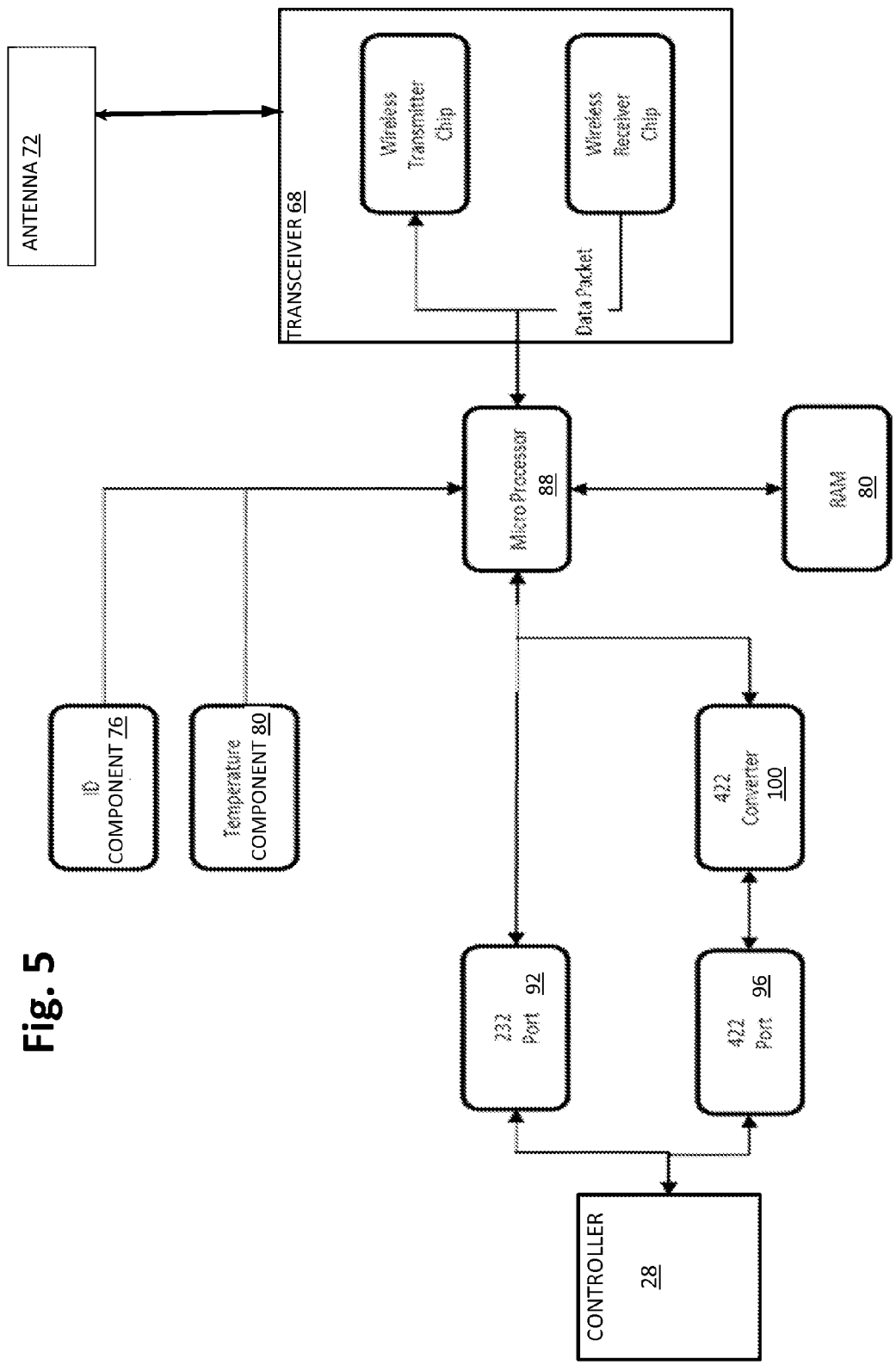
FIG. 5: is a block diagram showing the components of the wireless hub.

FIG. 5 illustrates the high level componentry of the hub 24. In addition to the antenna 72 and the transceiver 68, each hub 24 also includes:

(a) An ID component 76 which may be a programmable EPROM or other silicon based component for storing identification data uniquely identifying the hub 24 from all other hubs. The ID component 76 outputs, when requested by the micro-processor 88 (described below), the identification data to the micro-processor 88.

(b) A temperature measurement component 80 for outputting temperature values as requested by the micro-processor 88. Note that since this portion of the hub 24 is outside of the kiln, this temperature measurement component 80 measures the temperature outside the kiln, and such measurements can be useful for the controller 28 to control the wood/lumber drying process within the kiln, and in particular, control the activation of one or more of the heaters in the kiln, kiln intake and exhaust fans, and fans for circulating air within the kiln as one skilled in the art will understand.

(c) A data storage 84 (which may be persistent for storing data). This data storage 84 is used to store data packets (or data therefrom) received from the sensors 20.

(d) A micro-processor 88 for storing and accessing data packets received from sensors 20, and for generating, on request from the controller 28, aggregated data for sending to the controller 28. In particular, the micro-processor aggregates the following for sending to the controller 28: (1) one or more data packets from one or more sensors 20, (2) the unique hub identifier from the ID component 76 for uniquely identifying the hub, and (3) one or more temperature measurements from the temperature measurement component 80 (with corresponding timestamps).

(e) Various components used for digitally transmitting the aggregated data to the controller 28, such component may include one or more of: an RS-232 port 92, and an RS-422 port 96 together with a converter 100 for the RS-422 port as one skilled in the art will understand.

As mentioned previously, each hub 24 may be mounted outside its kiln in a location effective for communicating wirelessly with the hub's corresponding sensors 20 (e.g., within the kiln). Each hub 24 has an antenna 72 and a hub transceiver 68 that may be in the interior of the kiln so that the hub can better receive wireless transmissions from the corresponding sensors inside the kiln. Thus, as shown in FIG. 2, part of the hub 24 can be interior to the kiln (to which the hub is attached) and part of the hub can external to the kiln. The antenna 72 and wireless transceiver 68 captures the wireless transmission of the data packets from the wireless sensors 20 and provides the captured data packets to the hub's micro-processor 76. The micro-processor 76 stores the data packets in RAM 80 until the micro-processor 76 receives a request from the controller 28 to send the stored data packets to the controller. Once such a request is received by the hub 24, the micro-processor 76 retrieves the data packet(s) from the RAM 80, asks the ID component on board for the unique tag, obtains a reading from the local temperature component and then sends the aggregated data stream to the controller 28 via an RS422 or RS232 port.

FIG. 6 shows two high level flowcharts for limiting the number of wireless transmissions from each sensor 20 to its corresponding hub 24 and thereby conserving the batteries 54. The kiln environment is exceptionally harsh with temperatures regularly exceeding 200° F. for periods ranging from 16 to 48 hours or more. At these temperatures, the batteries 54 will experience a substantial reduction in life in comparison to a more typical battery environment as discussed above. For this reason, battery consumption must be conserved as much as possible.

Since the transceiver component 64 of each sensor 20 consumes the most sensor 20 battery power, a method for reducing the number of wireless transmissions without sacrificing critical data transfers to the corresponding hub 24 is provided in FIG. 6. In particular, the flowcharts of FIG. 6 provides the steps performed by the software executed by the micro-processor 40 or the controller 28 for comparing current sensor 20 readings to past readings (for the same sensor 20) in order to determine if a change in the moisture content data transmitted from this sensor warrants a more frequent or less frequent sensor wireless data transmission rate. Since what is deemed to be critical or/and not critical, changes per kiln operator, one or more setpoints for changing such transmission rates can be specified by, e.g., an operator (or automatically via computer instructions). Note that such setpoints may be dependent upon various wood/lumber drying characteristics, e.g., in-kiln temperature, sensor reading of resistance or capacitance, etc. Once such a setpoint is established, the sensor(s) 20 affected will only send updates to its corresponding hub 24 when the maximum or minimum corresponding conditions for the established setpoint(s) has been reached. As a fail-safe, there is a maximum time limit between transmissions that is allowed, so even if a sensor's generated output data has not changed, the sensor will still transmit wood/lumber drying related data packets to its corresponding hub 24.

Assuming the micro-processor 40 in the sensor 20, performs the steps of the flowcharts of FIG. 6, is the micro-processor 40 has a built-in timer (not shown) that counts the seconds (or fractional increments thereof) until the micro-processor 40 initiates a next collection of measurements/readings from the sensor components 44 through 56 (FIG. 2). The timer may have a default time interval of, e.g., 5 minutes between sending notifications so that the micro-processor 40 requests (in response to each notification) output data from the components 44 through 56. However, this time interval may be changed depending on the battery 56 remaining life, the wood/lumber drying measurements (or a change thereof), kiln operator input, and/or controller 28 computations of a new time interval. Accordingly, referring to the rightmost flowchart of FIG. 6, in step 604, once this timer has entirely counted down its time interval (or alternatively, if the timer is counting up to its time interval's end, then when the timer exceeds the time interval's end, as one skilled in the art will understand), the micro-processor 40 receives a "time interval expired" notification from the timer, and in response, the micro-processor 40 (step 608) sends a request to each of the components 44 through 56 (FIG. 2) to output their corresponding measurements/readings to the micro-processor 40. Upon receiving the measurements/readings, the micro-processor 40 (step 612) determines if it has exceeded the maximum time limit between wireless transmissions of data packets to its hub 24, wherein this maximum time limit is, in one embodiment, a time limit corresponding with one of the "fast mode" or the "slow mode" discussed hereinbelow with reference to FIG. 7. Note that the time interval used for determining the expiration in step 608 may be different from the maximum time limit. In particular, the time interval is substantially fixed and short enough so that the highest expected frequency of data packet generation and wireless transmission from the sensor 20 (equivalently, the smallest maximum time limit value) can be maintained. In particular, the time interval used in step 604 may be identical to the maximum time limit of the "fast mode" described hereinbelow.

Accordingly, if the maximum time limit of step 612 is exceeded, then the micro-processor 40 generates a new data packet from the newly received data obtained from components 44 through 56 (step 616). Subsequently, in step 620, this newly generated data packet is stored to a buffer (not shown) in the transceiver component 64 for transmission (step 624) to the corresponding hub's antenna 72 and wireless transceiver 68. Subsequently, in step 628, the timer is reset and the process starts over.

However, if in step 612, the maximum time limit between wireless transmissions is not exceeded, then in step 632, the steps of the leftmost flowchart of FIG. 6 are performed, wherein in step 636, the micro-processor 40 retrieves the previous measurement data obtained from the components 48 through 56 from its memory (not shown), and inputs the new and old measurements/readings (e.g., the capacitance, resistance, temperature and humidity values) to a calculation (step 640) selected by, e.g., the kiln operator (or the controller 28) to determine whether certain conditions, e.g., of the wood/lumber (between the metal plates 34 associated with the sensor 20), are satisfied. For example, such conditions may be for detecting a change in the capacitance and/or resistance of the wood/lumber being monitored. In particular, one or more of the three immediately following calculations may be performed by the micro-processor 40 to determine a change in capacitance or resistance and subsequently determine whether a certain conditions, using this change value, is satisfied (e.g., predetermined conditions and the particular "change" calculation may be specified by the operator and/or the controller 28):

1. Calculate a rate of change of the capacitance and/or resistance of the wood/lumber between the metal plates 34 associated with the sensor 20.
2. Calculate an absolute change, e.g., the positive value difference between the new value and the old value of the capacitance and/or resistance of the wood/lumber between the metal plates 34 associated with the sensor 20
3. Calculate the percent of change: the absolute difference between the new value and the old value divided by the old value of the capacitance and/or resistance of the wood/lumber between the metal plates 34 associated with the sensor 20.

However, it is also within the scope of the present disclosure that other measurements of wood/lumber capacitance and/or resistance may be calculated in additional to or instead of those of (1)-(3) immediately above. Moreover, selected calculations corresponding to in-kiln temperature and/or humidity can also be used in evaluating conditions related thereto. Thus, for temperature, one of the following calculations may be performed for a given temperature related condition:

4. Calculate a rate of change of the temperature of the wood/lumber in proximity to the sensor 20.
5. Calculate an absolute change, e.g., the positive value difference between the new value and the old value of the temperature of the wood/lumber in proximity to the sensor 20.
6. Calculate the percent of change: the absolute difference between the new value and the old value divided by the old value of the temperature of the wood/lumber in proximity to the sensor 20.

Similarly, selected calculations corresponding to in-kiln humidity can also be used in evaluating conditions related thereto. Thus, for humidity, one of the following calculations may be performed for a given humidity related condition:

7. Calculate a rate of change of the humidity of the wood/lumber in proximity to the sensor 20.
8. Calculate an absolute change, e.g., the positive value difference between the new value and the old value of the humidity of the wood/lumber in proximity to the sensor 20.
9. Calculate the percent of change: the absolute difference between the new value and the old value divided by the old value of the humidity of the wood/lumber in proximity to the sensor 20.

Once the selected calculations of (1)-(9) have been performed, then in step 644, the micro-processor 40 compares the results from the calculations of step 640 with one or more corresponding thresholds set by the operator (by the controller 28 without operator selection of such calculations) for determining if one or more of the certain conditions associated with these thresholds are satisfied. For example, for a threshold of 2 units corresponding to calculation an absolute change in the stack moisture content of step 640, if the result from the calculation is below the threshold, then it is presumed that the wood/lumber between the metal plates 34 associated with the sensor 20 is relatively dry. Additional such examples are as follows:

For a threshold of 5 degrees, corresponding to an absolute change in temperature, if the sensor 20 registers a change greater than this threshold, then it is presumed the ambient temperature in the kiln (e.g., at least proximate to the sensor 20) has sufficiently changed to warrant an update to the kiln operator.

For a threshold of 100%, corresponding to the percent of change in humidity, if the sensor 20 registers a change greater than this threshold, then it is presumed the ambient humidity in the kiln (e.g., at least proximate to the sensor 20) has sufficiently changed to warrant an update to the kiln operator.

Accordingly, if the micro-processor 40 determines that no threshold is crossed by the corresponding result (calculated in step 640) to which the threshold is compared thereby indicating that the corresponding condition for the threshold is not satisfied, then no data packet is generated for wireless transmission and the method of FIG. 6 starts over. However, if one of the thresholds is crossed, then steps 616 through 628 are performed for generating and wirelessly transmitting a new data packet to the corresponding hub 24. Thus, the wireless transceiver component 64 is only activated for performing wireless transmissions when the micro-processor 40 detects a change in one or more of the values output by the components 48 through 56 that are deemed significant to trigger the wireless reporting of this change to the corresponding hub 24 (and subsequently by this hub to the controller 28). Accordingly, the batteries 56 have their life extended by the process of FIG. 6.

Figure 7:
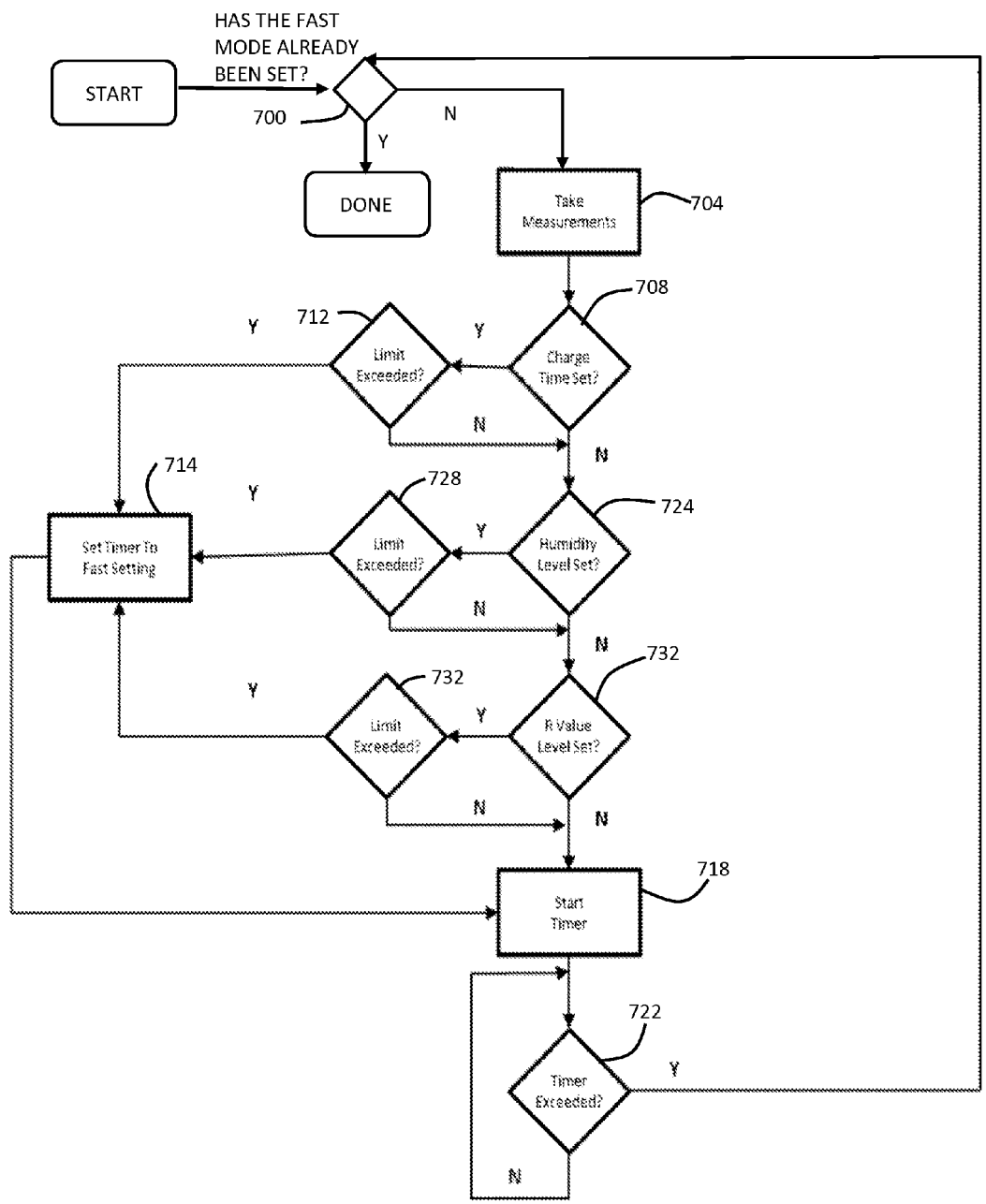
FIG. 7: is a flow chart describing the logic used to conserve battery power in a wireless sensor 20. In this case, the moisture readings are reduced.

Description of FIG. 7.

Referring now to FIG. 7, in a typical wood/lumber in-kiln drying cycle, the wood/lumber starts out very wet with moisture content in the 60%+ range by weight. Accordingly, a kiln operator(s) will typically initially ramp up the kiln temperature relatively high (e.g., in the range of 220° F. to 260° F.) and also adjust air speed inside the kiln in an effort to dry the lumber in a uniform manner. Readings from a moisture meter are typically used at this stage to guide this initial drying cycle as illustrated in FIG. 1. The operator(s) may also adjust some of the macro-conditions in the kiln (e.g., kiln vents, etc.) so that the wood/lumber finishes this initial drying cycle at 19% or less moisture content by weight. As the wood nears 19% in moisture content, the operator(s) may focus his/her attention on previously determined or historical correlations between characteristics of the drying wood/lumber and in-kiln environmental characteristics (such correlates referred to as a "drying curve") for achieving a targeted range of moisture content in the drying wood/lumber. For example, such correlations may relate, e.g., (i) the type of lumber, the amount of lumber in the kiln, and/or the stacking configuration of the lumber, with (ii) in-kiln temperature, in-kiln air circulation speed, kiln vent configurations, and/or the length of time at certain kiln drying configurations. Thus, the kiln operator(s) typically closely monitor each of the wood/lumber stack embedded sensors 20 in order to target a predetermined average lumber moisture content of, e.g., 19% or less. Moreover, as the moisture content to the drying wood/lumber gets close to the targeted lumber moisture content (e.g., 5% higher than the targeted lumber moisture content), the time between updated moisture related sensor values becomes more critical since one or two percent changes in wood moisture content can dramatically affect final product quality. Thus, such sensor 20 values need not be uniformly determined and transmitted for estimating lumber moisture content.

Thus, in order to manage and substantially lengthen the battery life of batteries 54 in sensors 20, a unique method for reducing the power consumed by the various components in such sensors has been developed and is disclosed herein with reference to FIG. 7. In particular, FIG. 7 provides a flowchart of the steps performed for setting the read rate (i.e., a wireless transmission rate) for each sensor 20 to either a "fast" wherein data packets are generated and wirelessly transmitted more frequently, or a "slow" mode wherein data packets are generated and wirelessly transmitted less frequently. That is, each of the fast mode and the slow mode has a corresponding time limit value which is indicative of the maximum time between wireless transmissions of data packets to the hub 24, wherein this maximum time is shorter for the fast mode, and longer for the slow mode (e.g., five minutes for the fast mode and fifteen to twenty times for the slow mode). Note, as indicated hereinabove, the maximum time limit used in step 612 of FIG. 6 is the maximum time limit of whichever of the fast and slow modes is currently being used by the micro-processor 40.

During the early phases of a drying cycle, each sensor 20 defaults to the "slow" mode in which data packet wireless transmissions are performed, e.g., every 15 minutes. When particular conditions are satisfied at a sensor 20, the micro-processor 40 of the sensor 20 switches to a "fast" mode wherein the wireless transmission rate of data packets increases to, e.g., every 5 minutes. In this way, battery 54 power consumed by all the components of the sensor 20 can be reduced since such components are activated less often during the initial portion of a drying cycle since the sensor is in slow mode.

In one embodiment, there are three possible trigger values to switch a sensor 20 from the slow mode to the fast mode. The three trigger values are of the following types:

i. Charge timer: A kiln operator (or the controller 28 exclusive of the operator(s)) can set a time (e.g., the number of hours) after the start of the drying wood/lumber drying process to switch from slow to fast mode, or possibly vice versa.

ii. Humidity level: The kiln operator can set a threshold corresponding to a particular relative humidity level in the kiln so that when this threshold is reached, the sensor 20 will switch from slow to fast mode. In the early phases of a kiln drying process, the humidity inside the kiln is very high as water is extracted from the wood/lumber and this extracted water disperses as moisture in the kiln air. Later in the wood/lumber drying process, there is less remaining water in the wood/lumber, and accordingly, the humidity levels in the kiln fall.

iii. R value level (i.e., an impedance threshold of the circuit 70 for the sensor 20): This value is a complex resistance value that can be used to judge the relative moisture content of the wood between the two metal plates 34 associated with the sensor 20. Low resistance indicates wet wood.

Each of these triggers may set remotely from the sensor 20 and transmitted wirelessly (via the sensor's corresponding hub 24) to the sensor for use by the sensor's micro-processor 40 in performing the flowchart of FIG. 7.

Accordingly, the steps of FIG. 7 determine the time interval used by the timer discussed hereinabove in describing FIG. 6.

That is, the time interval (either for fast mode, or slow mode) determined in FIG. 7 is used to determine when the timer expires in step 604 (FIG. 6)

Referring now to the steps of FIG. 7, for a given sensor 20 these step are described as follows:

Step 700: A determination is made as to whether the fast mode has already been set; i.e., the timer interval has been set to its shortest duration. If so, then FIG. 7 terminates since in the present embodiment, since once the fast mode is set it is set for the duration of the drying process.

Step 704: Assuming the fast mode has not yet been set, in the present step, the micro-processor 40 of the sensor receives measurements/readings from the sensor's components 48 and 52 (i.e., obtaining capacitance, resistance values of the circuit 70 (FIG. 2) having the sensor therein, and a relative humidity value output by the humidity component 52). Note that the capacitance and resistance values obtained are used to obtain the R value trigger type as shown in Appendix A.

Step 708: The micro-processor 40 determines whether a charge timer value has been communicated from the controller 28 to the sensor for currently being used as trigger for changing, e.g., from the slow mode to the fast mode.

Step 712: If a charge timer has been set, then the micro-processor 40 accesses an elapsed time since the kiln drying process commenced for determining whether the charge timer designated elapsed time has been exceeded. Note that the time at which in-kiln wood/lumber drying commenced can be communicated from the controller 28 to each of the sensors 20 in the kiln. Accordingly, as one skilled in the art will understand, each sensor's micro-processor 40 can use its own clock to iteratively determine elapsed times of the drying process.

Step 714: If the determination in step 712 is positive, then the maximum time limit for step 612 (FIG. 6) is set (by the micro-processor 40) to the value for the fast mode instead of the initial slow mode, e.g., the maximum time limit is reduced from, e.g., 15 minutes to 5 minutes Step 718: The timer (or some timer operably associated with the micro-processor 40) is activated for commencing to determine when a next instance of the maximum time limit is exceeded so that the micro-processor 40 (for this sensor 20) can be notified to provide a new data packet to the transceiver 64 for wirelessly transmitting to the corresponding hub 24 as per steps 615 through 624 of FIG. 6.

Step 722: After step 718, the present step is iteratively performed for determining whether the current maximum time limit is exceeded by its timer (assuming the timer is counting up to a designated time value indicative of the time interval offset, or alternatively, if this timer counts down the time interval, when the timer expires). Once the present step results in a positive determination, then step 700 is again performed.

Step 724: A determination is made as to whether a humidity level trigger has been set by the kiln operator (or the controller 28 independent of the operator).

Step 728: If a humidity level trigger has been set, then the micro-processor 40 accesses an the humidity level trigger value and a current humidity value obtained from the humidity component 52 for determining whether the humidity level trigger value has been exceeded by the current humidity value. If yes, then steps 714 through 722 are performed as described above. If not, then step 732 following is performed.

Step 732: A determination is made as to whether an R value level trigger has been set by the kiln operator (or the controller 28 independent of the operator).

Step 736: If an R value level trigger has been set, then the micro-processor 40 accesses an the R value level trigger value and a current impedance (for the sensor's circuit 70) obtained from the analog measurements components 48 for determining whether the R value level trigger value has been exceeded by the current impedance value. If yes, then steps 714 through 722 are performed as described above. If not, then steps 718 and 722 are performed.

FIG. 7 is particularly useful for kiln operators that want to increase the transmission of wireless sensor data packets after a certain number of hours has transpired, regardless of other ambient conditions. The reason that the operators are likely want such increases in transmission rate is that mills may want to begin a detailed examination of the drying rate early in the drying process in order to manage kiln fans and heating. Many mills believe such management improves final dried wood/lumber quality. Other mills may use such an increase in transmission rate as a backup in case other environmental conditions are not met. So, if a predetermined number of hours of a kiln wood/lumber drying process has transpired, no matter what, the mill may wish to increase the transmission rate to provide more data packets to the controller 28 and the operator.

The present disclosure has been presented for purposes of illustration and description. Further, the description herein is not intended to limit the present disclosure to the form disclosed herein. Consequently, variation and modification commiserate with the above teachings, within the skill and knowledge of the relevant art, are within the scope of the present disclosure. The present disclosure is further intended to enable others skilled in the art to utilize the present disclosure, or other embodiments derived therefrom, e.g., with the various modifications required by their particular application or uses of the present disclosure.

APPENDIX A

Introduction

This Appendix describes the use, operation and the circuit model of the sensor 20.

Sensor 20 Operation

There are two pushbuttons on the sensor 20, each with a red LED in the center.

POWER button (left) Holding this button for over 1 second toggles power on and off CONTROL button (right) Used to trigger a measurement, initiate calibration, clear flags, and enter or leave test mode.

The pushbuttons can sense "clicks" and "holds." A "click" is a quick button press (0.1 to 0.5 sec), and a "hold" is a single button press that lasts longer than 1 second. The number of sequential clicks is counted by the microcontroller and used to select various functions.

LED flashes are brief (20 ms) to minimize power consumption.

For the impedance determined by one of the analog measurements components 48, there are the following:

An analog input for impedance measurement.

An impedance output from the analog measurements component 48 for measuring impedance, e.g., from a sine wave generator output for such impedance measurements.

Sensor antenna which may be a ¼ wave wire antenna.

Control Button and LED

A control button (not shown) is provided on the sensor 20; the button is used as follows:

1 click Force immediate impedance measurement followed by 3 radio transmissions over the next 30 to 40 seconds.

4 clicks Initiate impedance calibration. A 10K calibration resistor must be connected across the measurement terminals. Calibration will not occur if the calibration resistor is not connected.

6 clicks Clear flag byte. This clears the over/under-temperature flags and low battery flag. The "calibration valid" flag is not affected.

The sensor 20 includes a control LED status light (not shown). Operation of the control LED is as follows:

1 Flash An impedance measurement has been made. Three random radio transmissions will follow to the corresponding hub 24 for wirelessly transmitting a data packet thereto.

2 Flashes Power just turned off

3 Flashes Power just turned on.

4 Flashes Calibration was successful.

6 Flashes Flag byte was cleared.

Long flash Just entered test mode.

Power Button and LED

The sensor 20 includes a power button (not shown); operation of this button is as follows:

Hold Toggle power on and off

If power is off, a hold of the power button causes the control LED to flash 3 times. Power to the sensor 20 is now on.

If power is on, a hold of the power button causes the control LED to flash 2 times. Power to the sensor 20 is now off.

There is a power LED on the sensor 20. The following are indicated by this LEC:

1 Flash Occurs every 4-5 seconds when power is on.

3 Flashes Just left test mode.

Radio Data Packets

The sensor 20 measures complex currents, battery voltage, and temperature every, e.g., 5 minutes (or as instructed by the controller 28) and transmits the results to its corresponding hub 24. In one embodiment, the transceiver component 64 sends one type of data packet, length 46 bytes, which contain the following information:

LEN (1 byte) Total data length in bytes, including this byte and CRC. Always 0x2E.

ID (4 bytes) Unique sensor 20 identifier.

Resistance (8 bytes) Eight measurements are provided:
R1H, R1L 1953.1250 Hz at high amplitude (R1H), 1953.1250 Hz at low amplitude (R1L);
R2H, R2L 2929.6875 Hz at high amplitude (R2H), 2929.6875 Hz at low amplitude (R2L);

Capacitance (8 bytes) Eight measurements are provided:
C1H, C1L 1953.1250 Hz at high amplitude (C1H), 1953.1250 Hz at low amplitude (C1L);
C2H, C2L 2929.6875 Hz at high amplitude (C2H), 2929.6875 Hz at low amplitude (C2L);

FLAGS (1 byte) Flag byte. Bits are as follows:

D0 1=low battery level (4.00V) occurred (for the batteries 54).

Cleared by the following actions to the sensor 20: power-on reset, pushbutton reset, and "clear flags" command issued by the controller 28 to the sensor 20.

D1 1=sensor 20 calibration invalid.
Cleared when calibration sensor 20 has been completed and is valid.

D2 1=fast (1-minute) impedance sampling by the sensor 20 in normal mode.
0=normal (5-minute) sampling of impedance by the sensor 20.
Can only be set or cleared when the sensor 20 is in test mode.

D3, D4 reserved, always 0 at this time.

D5 1=The temperature measurement at the sensor 20 dropped below −40 C. The controller 28 clears this data field by issuing a "clear flags" command to the sensor.

D6 1=temp exceeded 125 C. Cleared by "clear flags" command from the controller 28 to the sensor 20.

D7 1=temp exceeded 130 C. Cleared by "clear flags" command from the controller 28 to the sensor 20.

VBATT (2 bytes) Battery 56 voltage in units of 10 mV. This data field is an unsigned integer. Each measurement for this field is made during an impedance measurement (by the analog measurements component(s) 48) while battery current drain is at maximum.

TEMP (2 bytes) Temperature in degrees C. with 1-degree resolution at the sensor 20. This data field is a signed integer.

CRC (2 bytes) CRC. This is used by the controller 28 to verify that the serial data channel from the radio receiver has no errors. The radio receiver always checks that there are no radio channel errors.

Radio transmissions from the sensor 20 are repeated randomly three times with 11-14 seconds delay between, each transmission. Repeated transmission of the same data packet improves the probability of it being received by the sensor's corresponding hub 24 in the presence of multiple wireless transmissions from other sensors 20, radio fading, etc. In one embodiment, the corresponding hub 24 transfers each data packet instance received to the controller 28, the sensor ID, and a timestamp to avoid duplicately processing a data packet, or to detect that a measurement has been missed.

CRC Calculation

Data types used in the following code example are:

| | |
|---|---|
| UINT8 | unsigned integer 8-bit |
| UINT16 | unsigned integer 16-bit |
| UINT32 | unsigned integer 32-bit |

The following code takes the receiver packet buffer PktBuffer [ ] and calculates the 16-bit CRC:

```
UINT32 PktCRC;    // Shift register for CRC calculation.
                  // Bits 0x00ffff00 of PktCRC are the 16-bit CRC.
//***********************************************************
// Function pktGetCRC( )
// Calculate the CRC of the received packet.
//***********************************************************
UINT16 pktGetCRC (       // Return the 16-bit CRC result.
    UINT8 PktBuffer[ ])  // Received packet.
{
    UINT8 i, j;
    if (PktBuffer[0] != 0x2E)    // Exit of packet length is wrong.
        return 0;
```

```
    PktCRC = 0;             // Zero the CRC.
    j = PktBuffer[0] - 2;   // Number of bytes to process for CRC.
    for (i=0; i<j; i++) {   // Process all bytes before the message
                               CRC bytes.
            pktByteCRC(PktBuffer[i]);    // Update CRC for each byte.
    }
    pktByteCRC(0);          // Process 0's in place of the CRC bytes of
                               the packet.
    pktByteCRC(0);
    return (UINT16)( (PktCRC >> 8) & 0xFFFF ) ;
}
//***********************************************************
// Function pktByteCRC( )
// Update the CRC for one packet byte.
//***********************************************************
void pktByteCRC(         // Update the CRC for one byte of the packet.
    UINT8 byte)          // Data byte from packet.
{
    UINT8 i;
    PktCRC &= (UINT32)0x00ffff00;      // Clear low byte.
    PktCRC |= (UINT32)byte;            // Bring in the new data byte.
    for (i=0; i<8; i++) {              // Process 8 new bits into the CRC.
        PktCRC <<= 1;                  // Shift all.
        if (PktCRC & (UINT32)0x01000000)  // If 1 was shifted out,
            PktCRC ^= (UINT32)0x00102100;   // Apply inversions.
    }
}
```

The result should equal the 16-bit CRC from the received packet.

Impedance Calculation

The sensor 20 (more particularly, the analog measurement component 48 for obtaining impedance related values) applies to the circuit 70 a sine wave voltage to an induced predetermined impedance, and measures the resulting AC current of the circuit 70 through this impedance. The sensor 20 does not calculate the impedance itself. Rather, it makes a complex measurement of the AC current and provides the real and imaginary components thereof to the controller 28. The phase of the current is also measured relative to the phase of sine wave generator in the analog measurement component 48.

Complex current measurements are made at two different frequencies, 1953.125 Hz and 2929.6875 Hz as discussed above. At each frequency, measurements are made at a high amplitude (for impedances>=10K) and a low amplitude (for impedances 1K to 10K). Calibration measurements are also made at both frequencies and both amplitudes.

During calculations, the controller 28 checks the magnitude of the complex current. If the magnitude is too high during the high-amplitude measurement, the measurement circuit may have been clipping. In that case, the low-amplitude measurement must be used instead. In particular, if the high-amplitude measurement has a magnitude over 15500, use the low-amplitude measurement.

Figure 8:
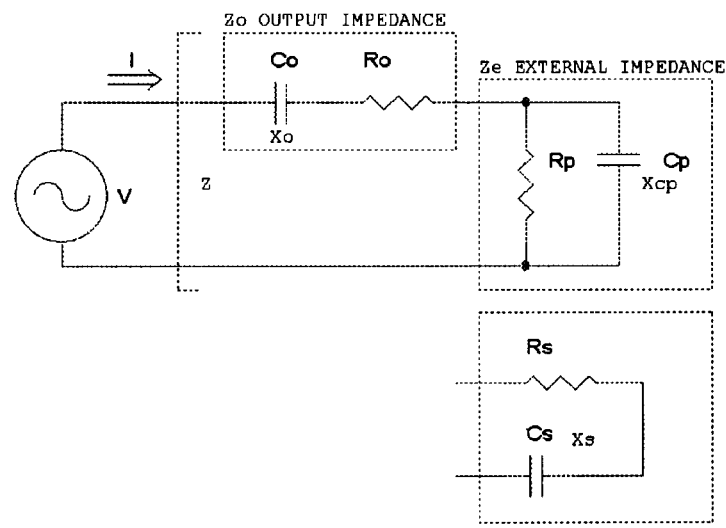
FIG. 8 is a circuit diagram.

The circuit diagram illustrated in FIG. 8 is used as a model for the circuit 70, wherein the external impedance in the diagram is the wood/lumber between the metal plates 34 associated with the sensor 20.

Referring to the circuit diagram illustrated in FIG. 8:
Fixed circuit values used are:
    Ro=2000 ohms Circuit output resistance
    Co=0.22 uF Circuit output capacitance
The measurement frequency value must be used when converting between reactance and capacitance. The impedance of a capacitor is defined as imaginary and negative, which means the current phasor through a capacitor is imaginary and positive (current leads voltage).

$Xc = -1/(2\pi FC)$ $C = 1/(2\pi F(-Xc))$ $Zc = -jXc$

Xc Capacitive reactance in ohms
Zc Complex impedance of a capacitor
C Cap in Farads
F Freq in Hz Parallel/Series conversions are required to calculate the external impedance Ze are as follows (the identifiers in the circuit diagram illustrated in FIG. 8 (and following): ending in "p" denote parallel measurements, and ending in "s" denote serial):

$Rp = (Rs^2 + Xs^2)/Rs$ $Xp = (Rs^2 + Xs^2)/Xs$ $Rs = RpXp^2/(Rp^2 + Xp^2)$ $Xs = Rp^2Xp/(Rp^2 + Xp^2)$

Rs, Cs External series equivalent resistance and capacitance
Xs External series equivalent reactance
Rp, Cp External parallel equivalent resistance and capacitance
$Xp = -1/(2\pi F\ Cp)$ External parallel equivalent reactance Equations used in the calculations are:

$Xo = -1/(2\pi FCo)$ Circuit output reactance $Zo = Ro + jXo$ Circuit Output Impedance $Ze = Rs + jXs$ External impedance $Ze = [RpXp^2/(Rp^2+Xp^2)] + j[Rp^2Xp/(Rp^2+Xp^2)]$ $Z = Zo + Ze$ Total impedance $I = V/Z$ Complex current $V = I\,Z$ Complex drive voltage Note, the calculations in this Impedance Calculation section may be performed by the analog measurements component(s) 48, and in one embodiment, by the impedance chip from Analog Devices, Inc.

Calibration

For calibration of the sensor 20, a 10K ohm resistor is connected and a calibration sequence is initiated. The sensor 20 measures the AC current through this resistor and stores the real and imaginary results. These calibration measurements are included in every data packet along with measurements for the unknown impedance.

During calibration, the controller 28 first uses the calibration current measurement, Ical, and the total calibration impedance, Zcal, to calculate the complex excitation voltage V as follows:

Rp, Cp External components connected in parallel during calibration $Ze = [RpXp^2/(Rp^2+Xp^2)] + j[Rp^2Xp/(Rp^2+Xp^2)]$ External impedance during calibration $Zcal = Zo + Ze$ Total impedance during calibration Ical Complex current measured during calibration
$V = Ical\ Zcal$ Complex drive voltage This complex V is constant and can be used in the calculations of unknown impedances. Four values of V may be calculated at each measurement frequency and at each amplitude. Capacitive reactance changes with frequency, and the internal phase shift of the sine wave source changes with amplitude.

The measurement units of I are not important, since V is calculated from I and so the units of V will be correct for calculating impedances in ohms as long as Zcal is calculated in ohms.

Measuring External Rp, Cp

Measurement involves connecting an unknown external Rp and Cp, measuring I, and using the known value of V to calculate Rp and Cp.

I Complex current measured

If abs(I)>15,500 then make the results Rp, Cp invalid. This will occur at high output amplitude when small external impedance is connected and indicates that the AD5933 A/D converter is clipping.

Z=V/I Total impedance with unknown Rp, Cp

If abs(I)<0.5 (complex I measurement is zero) then limit Z=1e8+0i to prevent overflows.

$Ze=Z-Zo$ External impedance with unknown Rp,Cp $Rs=re(Z)-Ro$ External series resistance $Xs=im(Z)-Xo$ External series reactance $Rp=(Rs^2+Xs^2)/Rs$ External parallel resistance Use the absolute value of Rp to cover cases where Rs is small and negative (re(Z) is close to Ro). Limit Rp to 10M ohms maximum to cover cases where Rs is very small.

$Xp=(Rs^2+Xs^2)/Xs$ External parallel reactance

Use the absolute value of Xp to cover cases where Xs is small and negative (im(Z) is close to Xo).

$Cp=1/(2\pi F(-Xp))$ External parallel capacitance

Limit Cp to the range 0.1 pF to 0.1 uF to cover cases where Xp is very large or small.

If the flag byte (described above) indicates that the sensor 20 is uncalibrated, then the Rp and Cp results are invalid.

Wireless Setup

Battery Installation and Sensor 20 Startup

The following procedure is for installing the batteries 56 in the sensor 20 and then activating the sensor.

Open the sensor 20 back cover and install two batteries 56. The batteries are both oriented in the same direction as marked on the battery holders. Incorrect installation will not damage the sensor 20, but it will not operate.

Press the "RESET" button on the PCB and check that the CONTOL LED flashes twice.

Hold the POWER button until the CONTOL LED flashes 3 times. Power is now turned on and the unit will transmit measurements every 5 minutes.

What is claimed is:

1. A method for monitoring the moisture content of a collection of wood members drying in a kiln, the kiln operable for applying heat, and air circulation for drying the collection to a specified moisture content,
    wherein a wireless sensor in operable contact with the wood collection for forming an electrical circuit with the wood, wherein the circuit additionally includes two spaced apart conductive plates positioned within the wood collection, and wherein the sensor and the circuit are configured to establish each of a capacitance and resistance of a water content of at least a portion of the collection, the portion residing between the spaced apart conductive plates; and
    wherein the sensor includes: (a) a wireless transmitter for wirelessly communicating with a stationary device, the stationary device for wirelessly receiving data from the sensor related to the water content of the portion of the collection, the data including measurements of the capacitance and resistance, and (b) one or more batteries for providing electrical power to the sensor;
    comprising performing the following steps by computational machinery:
    activating a timer for determining when a first time limit is exceeded;
    wirelessly transmitting a first instance of the data to the device, via the wireless transmitter, when the first time limit is exceeded;
    evaluating, based on the data, by performing one of: (i) a comparison of an elapsed time for drying the collection in the kiln with a predetermined elapsed time limit for drying the collection in the kiln, (ii) a comparison of a humidity in the kiln with a humidity threshold, or (iii) a comparison of an impedance for the portion of the collection with an impedance threshold;
    obtaining, based on a result of the evaluating, information for a second time limit different from the first time limit;
    using the information for activating the timer to determine when the second time limit is exceeded; and
    wirelessly transmitting a second instance of the data to the device, via the wireless transmitter, when the second time limit is exceeded;
    wherein for conserving the batteries, the first time limit is longer than the second time limit.

2. The method of claim 1, wherein the timer outputs a notification when the first time limit is exceeded.

3. The method of claim 1, wherein the first time limit is at least twice the duration of the second time limit.

4. The method of claim 1, wherein the using step includes replacing the first time limit with the second time limit.

5. The method of claim 1, further including the steps of:
    obtaining an instance of the data during the first time limit;
    determining a value indicative of a change between the instance and a previous instance of the data from a previous iteration of the method;
    comparing the value to a predetermined change related condition indicative of particular changes between instances of the data; and
    wirelessly transmitting the instance to the device, via the wireless transmitter, when the comparing step yields a first result indicative of the predetermined change related condition occurring between the one instance and the previous instance, and not wirelessly transmitting the instance when the comparing step yields a second result indicative of the predetermined change related condition not occurring between the one instance and the previous instance.

6. The method of claim 5, wherein the predetermined change related condition includes a threshold for determining whether a temperature change between the one instance and the previous instance is out of a range corresponding with the threshold, and wireless transmitting the one instance to the device when the temperature difference is out of the range.

7. The method of claim 5, wherein the predetermined change related condition includes a threshold for determining whether a humidity change between the one instance and the previous instance is out of a range corresponding with the threshold, and wireless transmitting the one instance to the device when the humidity difference is out of the range.

8. The method of claim 5, wherein the predetermined change related condition includes a threshold for determining whether a capacitance change in the circuit between the one instance and the previous instance is out of a range corresponding with the threshold, and wireless transmitting the one instance to the device when the temperature difference is out of the range.

9. The method of claim 5, wherein the predetermined change related condition includes a threshold for determining whether a resistance change in the circuit between the one instance and the previous instance is out of a range corresponding with the threshold, and wireless transmitting the one instance to the device when the temperature difference is out of the range.

10. The method of claim 1, wherein the evaluation of the predetermined condition comparing an elapsed time for drying the collection in the kiln with a predetermined elapsed time limit for drying the collection in the kiln.

11. The method of claim 1, wherein the evaluation of the predetermined condition comparing the humidity in the kiln with a humidity threshold.

12. The method of claim 1, wherein the evaluation of the predetermined condition comparing the impedance for the portion of the collection with an impedance threshold.

13. The method of claim 1, further including using the device as an intermediate wireless device for providing communications between a controller for controlling the drying of the collection in the kiln, the second wireless device for wirelessly communicating with a second sensor wirelessly.

14. The method of claim 1 further including using the device as an intermediate wireless device for providing communications between a controller for controlling the drying of the collection and the sensor, wherein the controller accesses data for locating the sensor within the collection or within the kiln.

15. The method of claim 14, wherein the controller selectively activates or deactivates the sensor dependent upon its location.

16. The method of claim 15, wherein the location of the sensor is relative to one or more other wireless sensors in the collection or in the kiln.

17. The method of claim 1, wherein the elapsed time is accounted from a commencement of the method.

18. A wireless sensor for monitoring the moisture content of a collection of wood members being dried in a kiln, the kiln operable for applying heat, and air circulation for drying the collection to a specified moisture content,
wherein the wireless sensor is in operable contact with the wood collection for forming an electrical circuit with the wood, wherein the circuit additionally includes two spaced apart conductive plates positioned within the wood collection, and wherein the sensor and the circuit are configured to establish capacitance and resistance of a water content of a portion of the collection, the portion residing between the spaced apart conductive plates; the sensor comprising:
one or more batteries for electrically powering the sensor;
a wireless transmitter for wirelessly communicating with a stationary device, the wireless communications including transmissions by the transmitter of data related to the water content of the portion of the collection, the data including measurements of each of the capacitance and resistance, measurements of the humidity in the kiln, and measurements of a temperature in the kiln;
a processor for iteratively: (i) obtaining one of the measurements of the capacitance, one of the measurement of the resistance, one of the measurements of the humidity, and one of the measurements of the temperature, and (ii) providing the one measurement of each of: the capacitance, resistance, humidity and temperature to the wireless transmitter for wirelessly transmitting as an instance of the data;
a timer for determining when a first time limit is exceeded;
wherein the wireless transmitter is configured to wirelessly transmit a first instance of the data to the device when the first time limit is exceeded;
wherein the processor is configured to evaluate based on the data b a performance one of: (i) a comparison of an elapsed time for drying the collection in the kiln with a predetermined elapsed time limit for drying the collection in the kiln, (ii) a comparison of a humidity in the kiln with a humidity threshold, or (iii) a comparison of an impedance for the portion of the collection with an impedance threshold;
wherein the processor is configured to obtain, based on a result of the performance, information for a second time limit different from the first time limit;
wherein the processor is configured to use the information for activating the timer to determine when the second time limit is exceeded;
wherein the wireless transmitter is configured to wirelessly transmit a second instance of the data to the device when the second time limit is exceeded;
wherein for conserving the batteries, the first time limit is longer than the second time limit.

19. The sensor of claim 18, wherein one of the instances of the data is obtained by the processor during the first time limit;
wherein the processor is configured to obtain a value indicative of a change between the one instance and a previous instance of the data from a previous iteration;
wherein the processor is configured to compare the value to a predetermined change related condition for identifying specific changes between instances of the data, and thereby obtain one of: a first result indicative of the predetermined change related condition occurring between the one instance and the previous instance, and a second result indicative of the predetermined change related condition not occurring between the one instance and the previous instance; and
wherein the wireless transmitter is configured to wirelessly transmit the instance to the device when the first result is obtained, and not wirelessly transmit the instance when second result is obtained.

20. The sensor of claim 18, further including a component that is configured to persistently store an identifier, wherein the identifier is retrieved from the component and included in each instance of the data for distinguishing wireless transmissions of the instances from wireless transmissions not originating with the sensor.

* * * * *

UNITED STATES PATENT AND TRADEMARK OFFICE
CERTIFICATE OF CORRECTION

PATENT NO. : 9,222,906 B2  
APPLICATION NO. : 13/934887  
DATED : December 29, 2015  
INVENTOR(S) : Patrick Youssi et al.

Page 1 of 1

It is certified that error appears in the above-identified patent and that said Letters Patent is hereby corrected as shown below:

In The Claims

Claim 18, column 30, line 16, replace "the data b a" with --the data by a--

Signed and Sealed this
Twenty-sixth Day of July, 2016

Michelle K. Lee
*Director of the United States Patent and Trademark Office*